(12) United States Patent
Ekes et al.

(10) Patent No.: US 9,115,842 B2
(45) Date of Patent: Aug. 25, 2015

(54) APPARATUS AND METHOD FOR INSPECTION OF UNDERGROUND PIPES

(75) Inventors: Csaba Ekes, Burnaby (CA); Boriszlav Neducza, Burnaby (CA)

(73) Assignee: Sewervue Technology Corp., Burnaby B.C. (CA)

( * ) Notice: Subject to any disclaimer, the term of this patent is extended or adjusted under 35 U.S.C. 154(b) by 594 days.

(21) Appl. No.: 12/980,009

(22) Filed: Dec. 28, 2010

(65) Prior Publication Data

US 2011/0196534 A1 Aug. 11, 2011

Related U.S. Application Data

(60) Provisional application No. 61/291,317, filed on Dec. 30, 2009.

(51) Int. Cl.
| | |
|---|---|
| *G01N 22/00* | (2006.01) |
| *F16L 55/48* | (2006.01) |
| *F17D 5/00* | (2006.01) |
| *G01D 21/00* | (2006.01) |
| *G01N 33/00* | (2006.01) |

(52) U.S. Cl.
CPC . *F16L 55/48* (2013.01); *F17D 5/00* (2013.01); *G01D 21/00* (2013.01); *G01N 33/00* (2013.01)

(58) Field of Classification Search
CPC ...... G01N 33/00; G01N 29/225; G01D 21/00
USPC ........................................................ 73/865.8
See application file for complete search history.

(56) References Cited

U.S. PATENT DOCUMENTS

| | | | |
|---|---|---|---|
| 5,454,276 A | 10/1995 | Wernicke | |
| 5,892,163 A | 4/1999 | Johnson | |
| 6,239,593 B1 | 5/2001 | Burkhardt et al. | |
| 6,243,657 B1 * | 6/2001 | Tuck et al. | 702/150 |
| 6,553,322 B1 * | 4/2003 | Ignagni | 702/34 |
| 6,768,959 B2 * | 7/2004 | Ignagni | 702/94 |
| 6,781,369 B2 | 8/2004 | Paulson et al. | |
| 6,986,294 B2 * | 1/2006 | Fromme et al. | 73/865.8 |

(Continued)

FOREIGN PATENT DOCUMENTS

| | | |
|---|---|---|
| DE | 4328031 A1 | 9/1992 |
| EP | 0654631 A1 | 11/1994 |
| JP | 08178907 | 12/1996 |
| WO | WO 2009029819 A1 | 3/2009 |

OTHER PUBLICATIONS

Duran et al., "State of the Art in Sensor technologies for Sewer Inspection" IEEE Sensors Journal, Apr. 2002, vol. 2, No. 2, pp. 73-81.

(Continued)

*Primary Examiner* — Hezron E Williams
*Assistant Examiner* — Rodney T Frank
(74) *Attorney, Agent, or Firm* — Knobbe, Martens, Olson & Bear LLP

(57) ABSTRACT

A system for inspecting an underground conduit from within comprises a data acquisition subsystem configured to be placed within the conduit and to move along at least a portion of the conduit to obtain data regarding the conduit. The system comprises a data storage subsystem configured to be placed within the conduit and to move along the conduit. The data storage subsystem receives and stores at least a portion of the data from the data acquisition subsystem for retrieval after the data acquisition subsystem has moved along the conduit.

25 Claims, 13 Drawing Sheets

(56) References Cited

U.S. PATENT DOCUMENTS

| | | | |
|---|---|---|---|
| 7,131,344 B2* | 11/2006 | Tarumi | 73/865.8 |
| 7,889,124 B2* | 2/2011 | Islam et al. | 342/357.2 |
| 2006/0266134 A1 | 11/2006 | MacMillan et al. | |
| 2007/0195712 A1* | 8/2007 | Thayer et al. | 370/254 |
| 2008/0164079 A1 | 7/2008 | Jacobsen | |

OTHER PUBLICATIONS

International Search Report and Written Opinion dated Jul. 7, 2011 of PCT Application No. PCT/IB2010/003470.

Australian Examination Report issued in Australian Application No. 2010337944, dated Jan. 14, 2014.

* cited by examiner

APPARATUS AND METHOD FOR INSPECTION OF UNDERGROUND PIPES

RELATED APPLICATIONS

This application claims priority from, U.S. Provisional Patent Application No. 61/291,317, filed Dec. 30, 2009, the entirety of which is expressly incorporated by reference herein and made a part of the present specification.

BACKGROUND

1. Field of the Invention

The present application generally relates to underground conduit inspection. More specifically, the present application relates to an improved underground conduit inspection system utilizing ground-penetrating radar.

2. Description of the Related Art

Ground-penetrating radar (GPR) is a real-time, non-destructive testing technique that can be used to locate targets embedded in concrete and to inspect the interior walls of concrete structures. GPR operates on the principle of transmission, reflection, and detection of short duration electromagnetic pulses from a transducer that is moved across the surface of the structure being analyzed.

GPR utilizes high frequency radio waves that can yield data with very high spatial resolution (e.g., on the order of centimeters) and the data can be acquired rapidly. Data collection can be continuous, allowing scanning of a two-foot by two-foot (60 cm by 60 cm) area in 15 minutes or less, or capturing several kilometers of continuous data in a few hours.

Current applications of GPR for structural engineers most commonly include locating spacing and depth of reinforcing steel, post tensioning cables or anchors, measuring rebar cover, mapping voids, and clearing areas prior to cutting, coring and trenching. GPR can also be a useful tool for seismic upgrades, road and bridge deck condition surveys, mapping delamination, or locating "lost" footings and/or utilities. See, e.g., Csaba Ékes, "Ground Penetrating Radar: Applications of GPR for Non-Destructive Concrete Testing and Structural Investigations," Construction Business, March/April 2007, pp. 48-49; and "Introduction to GPR," Terraprobe; "Csaba Ekes, "GPR: A New Tool for Structural Health Monitoring of Infrastructure," each of which is incorporated in its entirety by reference herein.

Structural applications can include addressing the integrity of the concrete itself, such as the presence of voids, cracks, or chemical alteration. Due to the less well defined character of such features, GPR applicability is not always predictable on these projects and interpretation of the results depends on the specific site conditions and on the experience of the technical personnel. Intrusive testing, such as drilling or coring, often accompanies GPR investigations in order to draw definitive conclusions.

SUMMARY

Certain embodiments provide a system for inspecting an underground conduit from within. The system may include a data acquisition subsystem configured to be placed within the conduit and to move along at least a portion of the conduit to obtain data regarding the at least a portion of the conduit. The system may further include a data storage subsystem configured to be placed within the conduit and to move along the conduit. The data storage subsystem is configured to receive and store at least a portion of the data from the data acquisition subsystem for retrieval after the data acquisition subsystem has moved along the at least a portion of the conduit. The data regarding the at least a portion of the conduit may include ground-penetrating radar data.

The data storage subsystem may store a substantial fraction of the ground-penetrating radar data. For example, the data storage subsystem stores at least thirty percent or more of the ground-penetrating radar data. In certain embodiments, at least a portion of the data stored by the data storage subsystem corresponds to a length of the at least a portion of the conduit, wherein the length is greater than at least ten meters. The data storage subsystem may be configured to store data at a rate of at least 10 kilobytes per second or more.

In certain embodiments, the data acquisition subsystem includes a body portion, a support portion configured to be in direct physical contact with the conduit or with material within the conduit so as to provide support for the body portion, and one or more antennas configured to be positionable in physical proximity to an inner surface of the conduit. The support portion may include at least one travel-facilitating member configured to provide locomotion of the data acquisition subsystem along a longitudinal axis of the conduit. The at least one travel-facilitating member may include at least one of the group consisting of: wheels, treads, tracks, hovercrafts, and flotation devices. The one or more antennas may be adjustably mounted to the body portion so as to controllably vary a distance between the one or more antennas and the inner surface of the conduit.

In certain embodiments, the data acquisition subsystem includes a body portion, a support portion configured to provide support for the body portion, at least one horn antenna, and a mirror configured to adjustably reflect a signal from the at least one horn antenna towards an inner surface of the conduit. The at least one horn antenna may comprise an ultra-wideband horn antenna. The data acquisition subsystem may comprise at least one camera configured to monitor the one or more antennas.

In certain embodiments, the system includes an above-ground control subsystem that provides at least one control signal to the data acquisition subsystem, wherein the data acquisition subsystem is responsive to the at least one control signal to control one or more aspects of the data acquisition subsystem. The data acquisition subsystem and/or the data storage subsystem may be tethered to the above-ground control system by a data conduit having a cross-sectional area of less than 0.2 square inches, and/or having a length of greater than 100 meters.

The data acquisition subsystem may include one or more cameras. The one or more cameras may include one or more wide-spectrum cameras. For example, the data acquisition subsystem may include at least one camera facing in a forward direction with respect to a direction of travel of the data acquisition device within the conduit, at least one camera facing in a direction substantially opposite to the forward direction Certain embodiments provide an apparatus for inspecting an underground conduit from within. The apparatus may include a data acquisition device configured to be placed within the conduit and to move along a first portion of the conduit to obtain data regarding the first portion of the conduit and a memory device configured to be positioned within the conduit and operationally coupled to the data acquisition device while positioned within the conduit, travel along a second portion of the conduit, and store at least a portion of the data from the data acquisition device for retrieval after the data acquisition device has moved along the first portion of the conduit. The memory device may be contained within a container that is liquid-tight. The memory device may be configured to provide wireless accessibility to data stored by the memory device. The container may comprise a lid configured to be manually removable to facilitate data transmission by providing physical access to the memory device. The second portion of the conduit may be coextensive with at least some of the first portion of the conduit.

Certain embodiments provide a method for inspecting an underground conduit from within. The method may include introducing a data acquisition device into the underground conduit, introducing a memory device into the underground conduit, moving the data acquisition device along a longitudinal axis of the underground conduit, obtaining data regarding at least a portion of the underground conduit, and storing at least a portion of the data on the memory device while the memory device is positioned within the underground conduit. The method may include transmitting a second portion of the data to a location outside of the underground conduit. The second portion of the data comprises to data provided by one or more cameras of the data acquisition device. At least one of the one or more cameras may be a wide-spectrum camera.

In certain embodiments, an antenna mount system is provided which is configured to hold a ground-penetrating radar (GPR) antenna in proximity to an inner surface of a pipe to be inspected while the GPR antenna is moved along the inner surface during inspection of the pipe. The system comprises a support structure configured to adjust a position of the GPR antenna in response to a force applied to the GPR antenna by the surface. In response to a drag or friction force between the surface and the GPR antenna, the support structure adjusts the position of the GPR antenna substantially along a direction of the drag or friction force. For example, where inspection of the pipe comprises orienting the GPR antenna relative to a longitudinal axis of the pipe and moving the GPR antenna in a first direction along the surface, a drag or friction force is applied by the surface to the GPR antenna in a second direction substantially opposite to the first direction. In response to the drag or friction force, the support structure adjusts the position of the GPR antenna substantially along the second direction. In certain such embodiments in which inspection of the surface further comprises maintaining the orientation of the GPR antenna relative to the longitudinal axis of the pipe and moving the GPR antenna in the second direction along the surface, a drag or friction force is applied by the surface to the GPR antenna in the first direction, and the support structure adjusts the position of the GPR antenna substantially along the first direction.

In certain embodiments, a method of acquiring underground pipe inspection data is provided. The method comprises providing a robot with one or more ground-penetrating radar (GPR) antennas. The method further comprises placing the one or more GPR antennas at corresponding first positions along the periphery of an inside surface of a pipe. The method further comprises obtaining inspection data using the one or more GPR antennas at the corresponding first positions as the robot travels in a first direction substantially along a longitudinal axis of the pipe being inspected. The method further comprises repositioning the one or more GPR antennas to be at corresponding second positions. The method further comprises obtaining inspection data using the one or more GPR antennas at the corresponding second positions as the robot travels in a second direction substantially along the longitudinal axis of the pipe being inspected, the second direction substantially opposite to the first direction.

DETAILED DESCRIPTION

Figure 1:
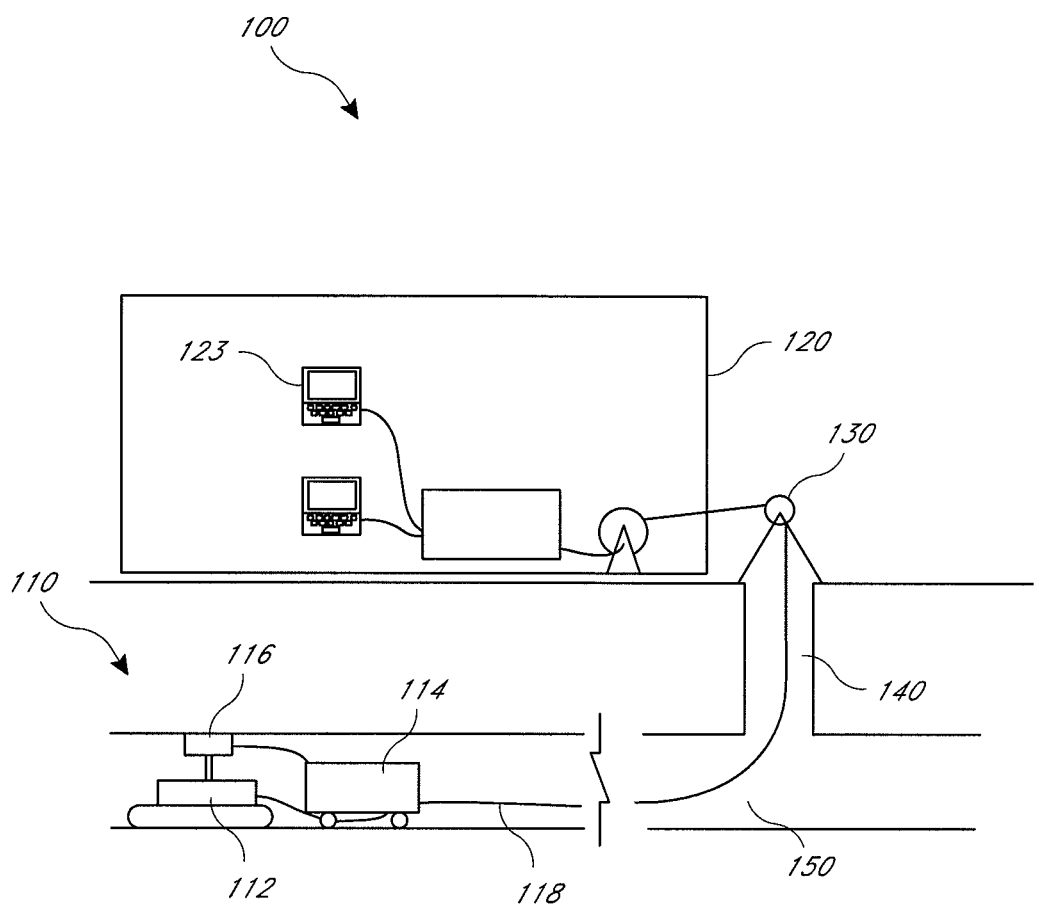
FIG. 1 illustrates an example underground conduit inspection system in accordance with certain embodiments described herein.

Although several embodiments, examples, and illustrations are disclosed below, it will be understood by those of ordinary skill in the art that the invention described herein extends beyond the specifically disclosed embodiments, examples and illustrations and includes other uses of the invention and obvious modifications and equivalents thereof. Embodiments are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments. In addition, embodiments can comprise several novel features and no single feature is solely responsible for its desirable attributes or is essential to practicing the inventions herein described.

The various embodiments provide novel methods, systems and devices for electromagnetic scanning. The methods, systems, and devices are disclosed in the context of devices and methods utilizing ground penetrating radar (GPR) because they have particular utility in this context. The embodiments disclosed herein, however, can also be used in other contexts, such as, for example, but without limitation, sonar, impact-echo, ultrasound and other mechanical wave sources and detectors, electric, magnetic, laser, gas detector, infrared and other electromagnetic transmitters and receivers, as well as other contexts.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

The term "robot" as used herein is a broad term, and unless otherwise indicated, the term can include any device with at least one moveable member, such movement being controllable either automatically, or by a user, computer system, or the like. While many of the methods, systems, and apparatuses disclosed below incorporate "robots," the term "robot" is not meant to be limiting in any way, and may refer to any suitable device for implementing the methods, systems, and apparatuses disclosed below.

The term "inspection data" is interpreted broadly to include any data provided by the data acquisition subsystem, including but not limited to, antenna data and camera data. In certain embodiments, all of the inspection data is stored within the data storage subsystem (e.g., on the memory device) and none of the inspection data is transmitted to an above-ground control system. In certain other embodiments, a first portion of the inspection data is transmitted to an above-ground computer system outside of the pipe during the inspection, either directly or via the data storage subsystem, and a second portion of the inspection data is stored during the inspection (e.g., within the data storage subsystem on the memory device). For example, some or all of the data provided by one or more cameras may be transmitted to an above-ground computer system, while none of the data provided by one or more GPR antennas is transmitted to an above-ground computer system, but is instead stored within the data storage subsystem. In one such example, during the inspection, one or more camera images are transmitted to the above-ground computer system, and control commands are sent from the above-ground computer system to the pipe inspection system within the pipe (e.g., to control the pipe inspection system so as to avoid obstacles within the pipe shown by the camera images). As another example, some or all of the data provided by one or more cameras, as well as a portion of the data provided by one or more GPR antennas (e.g., a small portion used for diagnostic purposes), may be transmitted to an above-ground computer system, while the majority of the data provided by the one or more GPR antennas is stored within the data storage subsystem.

While certain embodiments are described below for inspecting underground conduits or pipes, the terms "underground," "conduit," and "pipe" are not meant to be limiting. For example, certain embodiments described herein may be used for inspection of conduits or pipes that are only partially underground, or that are not underground at all. In addition, certain embodiments described herein may be used for inspection of conduits, pipes, cavities, channels, rooms, walls, or other structures comprising various materials (e.g., concrete) with structural supports (e.g., rebar) embedded within.

Conduit Inspection System

In certain embodiments described herein, a conduit inspection system is provided. The system is configured to move within a conduit substantially along a longitudinal axis of the conduit to inspect one or more portions of the conduit and/or surrounding materials. The system comprises a data acquisition subsystem and a data storage subsystem. The data acquisition subsystem comprises one or more ground-penetrating radar (GPR) antennas positioned within the conduit during the inspection. The one or more GPR antennas are configured to emit GPR signals and to detect GPR signals reflected from the one or more portions of the conduit and/or the surrounding materials. The detected GPR signals reflected from the one or more portions of the conduit and/or the surrounding materials comprise inspection data indicative of the one or more portions of the conduit and/or the surrounding materials. In certain embodiments, the system implements impact-echo technology, in which sound waves are sent into a wall of the conduit and the rebound, or echo, is measured in order to locate voids within or outside the wall.

The data storage subsystem comprises a memory device operatively coupled to the data acquisition subsystem and located within the conduit during the inspection (e.g., proximate to the data acquisition subsystem). The data storage subsystem is configured to receive the inspection data from the data acquisition subsystem.

During the inspection, the system is configured to transmit a first portion of the inspection data to a computer system outside of the conduit, either directly, or via an in-conduit computer system. During the inspection, the system is configured to transmit a second portion of inspection data to an in-conduit computer system. The memory device is configured to store portions of the inspection data that is not transmitted to the computer system outside of the conduit. The data storage subsystem is further configured to provide operational access to the memory device and to the stored portions of the inspection data upon removal of the memory device from within the conduit after the inspection of the one or more portions of the conduit and/or the surrounding materials. In an embodiment, a screen image of the in-conduit computer is transmitted to a computer system outside of the conduit. In an embodiment, control commands are sent from a computer system outside of the conduit to the in-conduit computer system.

With reference to FIG. 1, there is shown an example underground conduit inspection system 100 in accordance with certain embodiments described herein. The system 100 comprises an underground conduit-inspecting device 110 and an above-ground control subsystem 120. The underground conduit-inspecting device 110 may include a data acquisition subsystem 112 and a data storage subsystem 114. While FIG. 1 shows the data storage subsystem 114 as a separate component from the data acquisition subsystem 112 (e.g., the data acquisition subsystem 112 comprising a motorized robot and the data storage subsystem 114 comprising a trailer pulled along the conduit by the robot), in certain embodiments, the data storage subsystem 114 and the data acquisition subsystem 112 are integral with one another.

In certain embodiments, the conduit inspection system 100 implements Light Detection and Ranging (LIDAR), Laser Detection and Ranging (LADAR), or any other suitable sensing, detection, or inspection technology for the purpose of obtaining and analyzing data indicative of the state of a conduit or pipe, or characteristics thereof.

In certain embodiments, the data acquisition subsystem 112 comprises a robot with ground penetrating radar (GPR) illumination and detection capability. The underground conduit-inspecting device 110 may be introduced into an underground cavity or conduit 150, such as a sewer conduit, via a surface ingress channel 140, such as a manhole. In certain such embodiments, the robot is motorized and controllable by the above-ground control subsystem 120 to controllably move within the underground cavity or conduit 150 (e.g., conduit) and to acquire data regarding the one or more walls of the conduit 150 and/or the surrounding material.

In certain embodiments, the data acquisition subsystem 112 comprises one or more GPR antennas 116 configured to be positioned in proximity to the inner surface of the conduit wall to be inspected. The one or more GPR antennas 116 may be, for example any suitable radio antenna, such as dipole antennas, or any other suitable antenna. Example GPR antennas compatible with certain embodiments described herein include, but are not limited to, shielded and HF shielded antennas from Mala Geoscience, headquartered in Mala, Sweden, such as the 1.0 GHz, 1.2 GHz, 1.6 GHz and 2.3 GHz antennas (more information at http://www.malags.com/Solutions/Products/Full-Range-Series/Modules/Antennas.aspx). The system could also incorporate antennas from other manufacturers, such as Geophysical Survey Systems, Inc. (GSSI), headquartered in Salem, N.H., Sensors & Software, Inc., headquartered in Ontario, Canada, or Ingegneria dei Sistemi SpA (IDS), headquartered in Pisa, Italy, in the medium to high frequency range: 250 MHz to 2.6 GHz, as well as horn antennas in the 1 GHz to 4 GHz range, or other suitable antennas. In certain embodiments, the GPR antennas utilize electromagnetic waves with frequencies greater than 2 GHz (e.g., greater than or equal to 2.6 GHz). In general, the resolution of a GPR system increases with increasing frequency, however, the maximum distance or depth from the GPR antenna at which reliable data is obtained decreases with increasing frequency. See, e.g., "Csaba Ékes, "GPR: A New Tool for Structural Health Monitoring of Infrastructure," incorporated in its entirety by reference herein. In certain such embodiments, the frequency of the GPR antennas is selected to provide sufficient resolution to provide reliable data at a desired maximum depth.

Figure 12A:
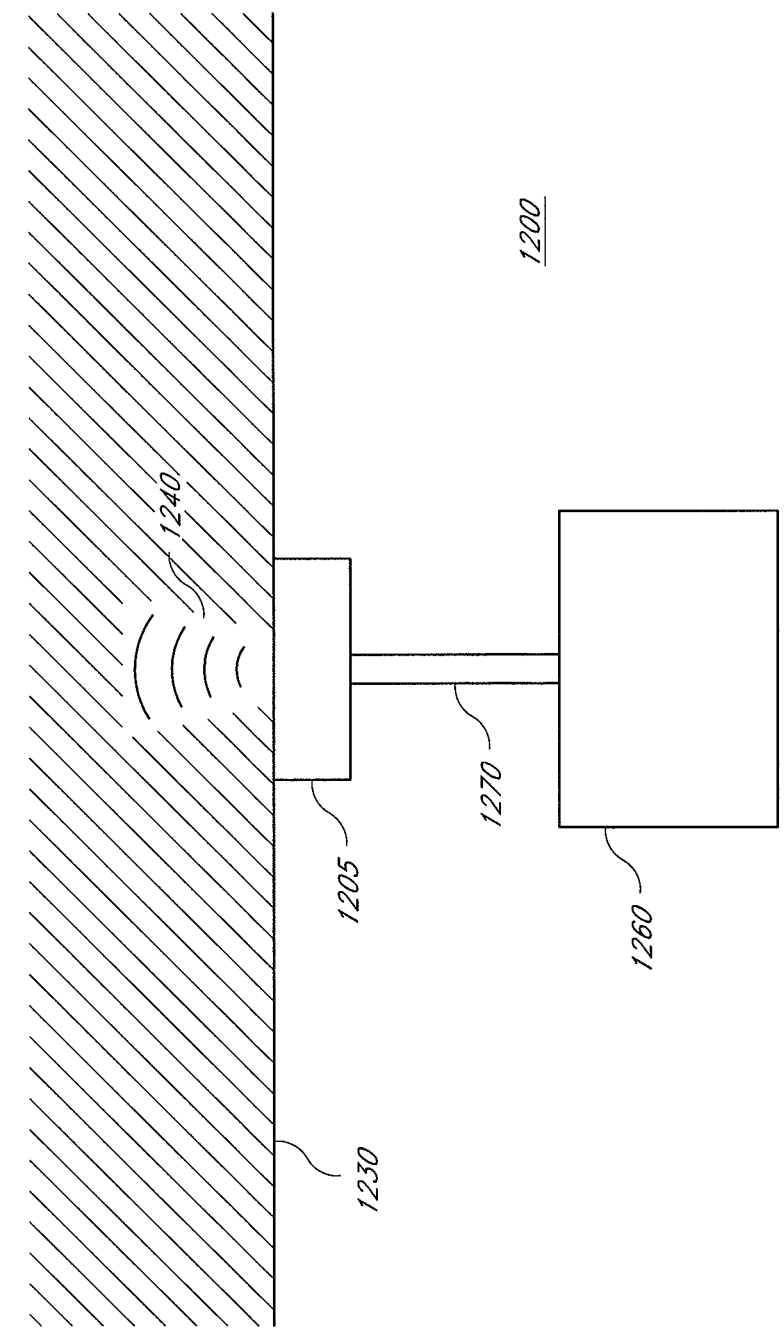
FIGS. 12A and 12B illustrate example antenna configurations for an underground conduit inspection device in accordance with certain embodiments described herein.

FIG. 12A illustrates an example antenna configuration that may be incorporated into a data acquisition subsystem 112. The embodiment depicted in FIG. 12A includes a GPR antenna 1205 configured to direct a signal 1240 in the direction of a wall 1230 of an underground conduit 1200. The signal 1240 penetrates the wall 1230 of the conduit 1200 and a reflected portion of the signal reflected by the wall 1230 and received by the GPR antenna 1205 provides data relating to the condition or characteristics of the wall 1230 or its surroundings. The GPR antenna 1205 may have any suitable configuration. For example, the GPR antenna 1205 may include a guide plate to facilitate movement along the wall 1230 of the conduit 1200, and may be configured to operate at any suitable frequency, as described above. Positioning the GPR antenna 1205 in close proximity to the wall 1230 of the conduit 1200 may reduce the attenuation and unwanted reflection of the signal 1240 at the surface of the wall 1230, and therefore the accuracy and/or relevance of data obtained therefrom.

The GPR antenna 1205 may be supported by one or more support members 1260, 1270, or may be physically positioned or supported by hand. In certain embodiments, the GPR antenna 1205 is supported by a body portion 1260 and an adjustable arm member 1270.

Figure 12B:
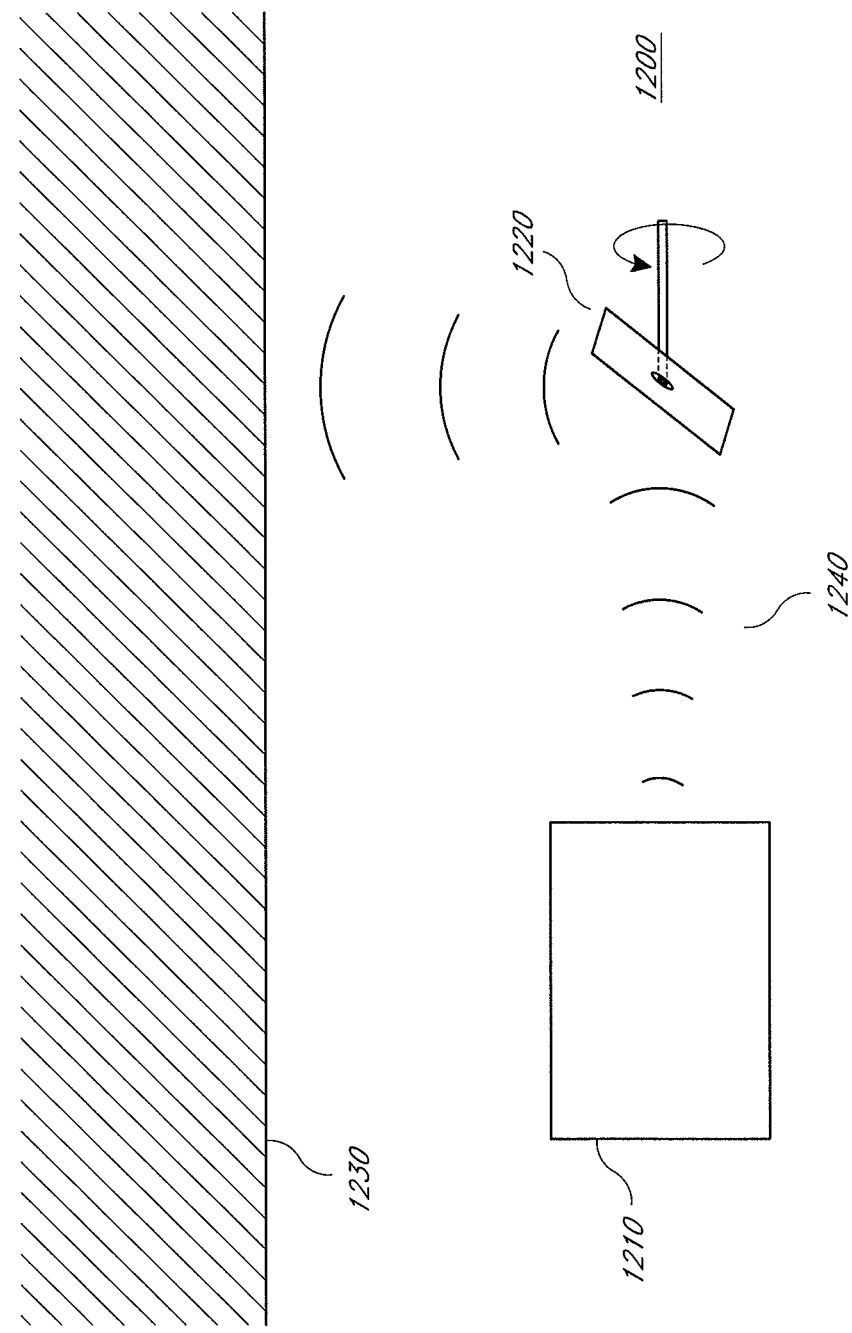

FIG. 12B illustrates an example antenna configuration that may be incorporated into a data acquisition subsystem 112. The embodiment depicted in FIG. 12B includes a horn antenna 1210, or other directive antenna configured to direct a signal 1240 in the direction of a radar-reflecting element 1220 (e.g., a mirror, as shown in FIG. 12B). The radar-reflecting element 1220 serves to deflect the transmitted signal 1240 in the direction of a wall of an underground conduit, as well as to deflect reflections of the signal 1240 reflected by the wall 1230, or by matter outside the wall 1230, back in the direction of the horn antenna 1210. The horn antenna 1210 may have any suitable configuration. For example, the horn antenna 1210 may include a flaring metal waveguide, generally in the shape of a horn.

Horn antennas compatible with certain embodiments described herein can provide the advantages of moderate directivity or gain, low standing wave ratio (SWR), simple construction and adjustment, as well as broad bandwidth (e.g., greater than 500 MHz). For example, a horn antenna incorporated into an underground conduit-inspection system 100 may transmit ultra-wideband (UWB or ultraband) signals, which use a large portion of the radio spectrum. UWB, which can be used at low energy levels, may be suited for underground conduit inspection due to the relative short transmission distance often associated with underground conduit inspection.

As illustrated in FIG. 12B, a mirror 1220, or other radar reflection or deflection device, may be used to direct the transmitted signal 1240 from the directive horn antenna 1210 to an inner conduit wall 1230. The mirror 1220 may be configured to rotate or to be otherwise adjusted such that the direction of deflection of the transmitted signal 1240 and the reflected signal received from the wall 1230 may be altered. In certain embodiments, the mirror 1220 rotates about an axis generally parallel to the longitudinal axis of the conduit 1200, thereby allowing inspection of a conduit at various points along a circumferential band or region of the conduit wall 1230.

Figure 2:
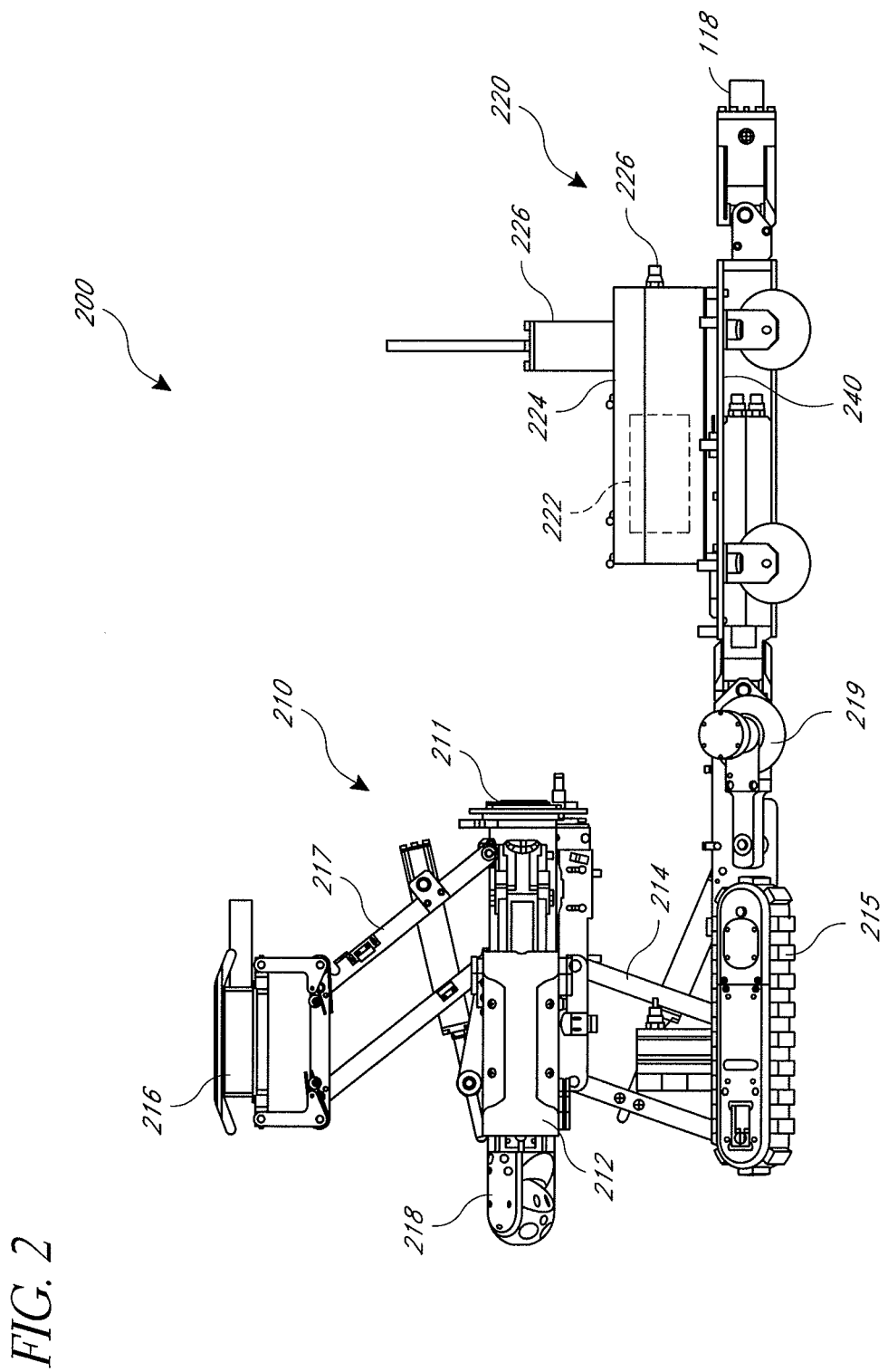
FIG. 2 provides a profile view of an example underground conduit inspection device in accordance with certain embodiments described herein.
Figure 3:
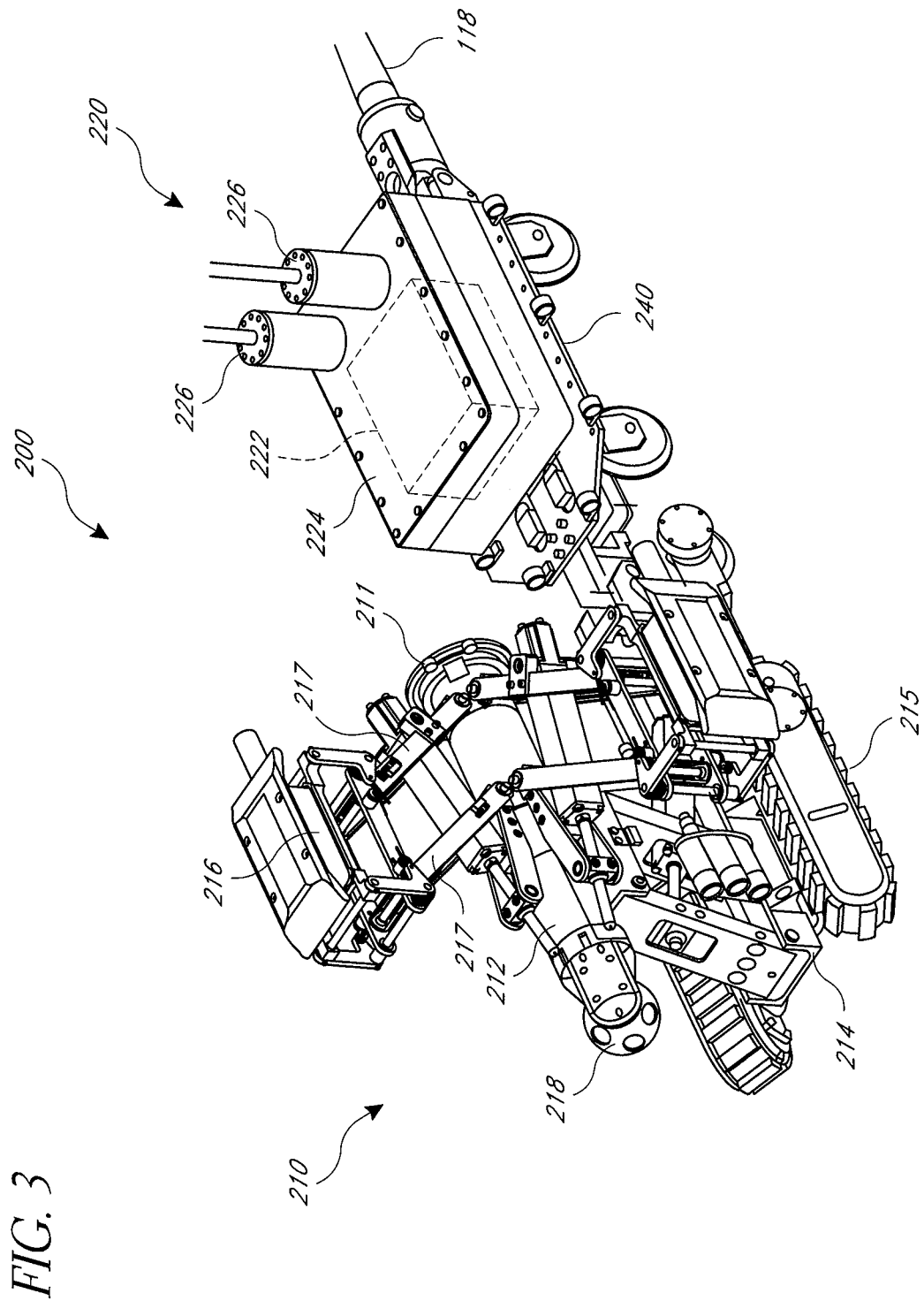
FIG. 3 provides a perspective view of an example underground conduit inspection device in accordance with certain embodiments described herein.

With reference to FIGS. 1-3, the data acquisition subsystem 112 may further includes one or more video or image acquisition devices (e.g., cameras 218) which are configured to provide visual images (e.g., still images or video images) of the inner periphery of the underground conduit 150, in the visible and invisible (e.g., infrared, ultraviolet, etc.) wavelength domain. The one or more video or image acquisition devices may be utilized in a closed-circuit television subsystem. In certain embodiments, the data acquisition subsystem 112 includes one or more wide-spectrum cameras. Examples of cameras compatible with certain embodiments described herein include, but are not limited to, Inuktun Spectrum 90 pan and tilt cameras, manufactured by Inuktun Services, Nanaimo, BC, Canada. In certain embodiments, at least one of the one or more cameras 218 is controllable from the above-ground control subsystem 120 to adjust the configuration or operation of the at least one camera 218 (e.g., viewing direction, focus, aperture). In certain embodiments, the one or more cameras 218 includes a first camera configured to be pointed in a first direction and a second camera configured to be pointed in a second direction generally opposite to the first direction. For certain such embodiments, as the data acquisition subsystem 112 is moved in the first direction along the conduit 150, the first camera can provide images of the conduit 150 along the direction of movement, and/or visual information about the GPR antenna position and coupling with the conduit wall. Upon reversing the direction of movement, as the data acquisition device 112 is moved in the second direction, the second camera can provide images of the conduit along the direction of movement.

The data acquisition subsystem 112 may include a dedicated camera for monitoring the one or more GPR antennas (e.g., a camera positioned to monitor the position or operation of at least one of the one or more GPR antennas). Use of a dedicated camera for such purposes can aid in the remote control positioning and operation of the GPR antennas. In certain embodiments, a dedicated camera may be positioned such that it constantly monitors one or more GPR antennas 116. Other dedicated cameras for particular purposes may also be used, such as, for example, to aid in the control of antenna positioning.

In certain embodiments, the data acquisition subsystem 112 comprises one or more light sources that may be controllable by the above-ground control subsystem 120 to illuminate the inner cavity of the conduit 150 to be imaged by the one or more cameras. For example, the data acquisition subsystem 112 may comprise one or more electroluminescent light sources (e.g., light-emitting diode ("LED") light sources), incandescent light sources (e.g., halogen lamps), gas discharge light sources (e.g., fluorescent lamps), or other types of light sources. In certain embodiments, auxiliary lighting carried by the data acquisition subsystem 112 comprises one or more LEDs, while camera lights comprise one or more halogen incandescent bulbs.

In an embodiment, the above-ground control subsystem 120 includes one or more displays configured to provide the user with a view within the underground cavity 150. For example, during operation, the one or more cameras may transmit images obtained within the conduit to a display in the above-ground control subsystem 120, and a user can use these images to controllably adjust the movement or configuration of the data acquisition subsystem 112 within the conduit 150 (e.g., to avoid protrusions, obstructions, holes, or other features which would impede the operation or movement of the data acquisition subsystem 112). In another embodiment, visual images may be transmitted to a remote location.

In an embodiment, one or more cables 118 connect the underground conduit-inspection device 110 with the above-ground control subsystem 120 to send and/or receive signals between the underground conduit inspection device 110 and the above-ground control subsystem 120. The one or more cables 118 may include optical fiber and/or electrical cables, copper cables, co-axial cables, wires, and the like, or combinations thereof. In an embodiment, the underground conduit-inspection device 110 may send and/or receive signals to/from the above-ground control subsystem 120 at least partially via one or more wireless communication devices. In an embodiment, a pulley system 130 facilitates the movement of the one or more cables 118 between the above-ground control subsystem 120 and the underground conduit-inspection device 110.

In certain embodiments, the one or more cables 118 provide one or more signal conduits for communication between the above-ground control subsystem 120 and the underground conduit-inspection device 110 and/or power from the above-ground control subsystem 120 to the underground conduit-inspection device 110. In certain embodiments, the one or more cables 118 comprise one or more copper conductors for transmission of signals, power, or both between the underground conduit-inspection device 110 and the above-ground control subsystem 120. For example, a 16-gauge copper conductor may be used for power transmission. The one or more cables 118 may include one or more video transmission cables. Video transmission cables may, for example, be of 24-gauge twisted pair construction. In certain embodiments, the one or more cables 118 include fiber optic cables for data transmission.

In certain embodiments, the one or more cables 118 include one or more signal conduits having a total cross-sectional area of less than 0.2 square inches. For example, in certain embodiments, the total cross-sectional area of the one or more signal conduits is approximately 0.1385 square inches. In contrast, conventional systems can include one or more signal conduits having a total cross-sectional area of 2.5 square inches or larger. In certain embodiments, the one or more cables 118 have a length of greater than 100 meters. Conventional systems may include cables no longer than 75 meters.

In an embodiment, the above-ground control subsystem 120 includes a GPR control subsystem and a robot control subsystem. In an embodiment, the GPR control subsystem includes devices for controlling the configuration and operation of one or more GPR antennas 116 mounted on the data acquisition subsystem 112 (e.g., on the robot). In an embodiment, the robot control subsystem includes devices for controlling the direction and speed of travel of the data acquisition subsystem 112. In certain embodiments, the GPR control subsystem and the robot control subsystem are separate from one another, while in certain other embodiments, the GPR control subsystem and the robot control subsystem are integral with one another.

Both or either of the GPR control subsystem and robot control subsystem may be executed on a computing system by a central processing unit discussed further below. The computing system can comprise a fixed system or a mobile device that is in communication with one or more computing systems and/or one or more data sources via one or more networks. The computing system may be used to implement the underground conduit-inspection system 100.

The computing system of certain embodiments comprises one or more commonly available input/output (I/O) devices and interfaces, such as a keyboard, roller ball, pen and stylus, mouse, touchpad, trackball, voice recognition system, pre-designated switches or buttons, and printer. In one embodiment, the I/O devices and interfaces comprise one or more display devices, such as a monitor, that allows the visual presentation of data to a user. More particularly, a display device provides for the presentation of GUIs, application software data, and multimedia presentations, for example. In the embodiment of FIG. 1, the I/O devices and interfaces also provide a communications interface to various external devices 123 which the user can access to monitor and/or to control the various components of the underground conduit inspection device 110. The computing system may also comprise one or more multimedia devices, such as speakers, video cards, graphics accelerators, and microphones, for example.

In one embodiment, the computing system comprises a central processing unit ("CPU"), which may comprise one or more microprocessors (e.g., multicore microprocessors). The computing system further comprises a memory, such as random access memory ("RAM") for temporary storage of information and/or a read only memory ("ROM") for permanent storage of information, and a mass storage device, such as a hard drive, diskette, flash memory, or optical media storage device. The computing system may run on a variety of computing devices, such as, for example, a server, a web-enabled user access point, a personal computer, a mainframe computer, a laptop computer, a cell phone, a personal digital assistant, and so forth. The computing system may be controlled and coordinated by operating system software which controls and schedules computer processes for execution, perform memory management, provide file system, networking, and I/O services, and provide a user interface, such as a graphical user interface ("GUI"), among other things.

In one embodiment, the processes, systems, and methods illustrated herein may be embodied in part or in whole in software that is running on a computing device. The computing device may include one or more components and/or modules operatively connected to one another. The connections may use a standards-based bus system, and may be direct physical connections, virtual connections, physical network connections (for example, using a telephone line or the like), and/or wireless network connections. Such a computing device may have a browser module implemented as a module that uses text, graphics, audio, video, and other media to present data and to allow interaction with data via the network. In general, the word "module," as used herein, refers to logic embodied in hardware or firmware (such as an EPROM), or to a collection of software instructions, possibly having entry and exit points, written in a programming language. The modules described herein can also refer to logical modules that may be combined with other modules or divided into sub-modules despite their physical organization or storage.

The data acquisition device 110 may include any of a number of tools for assisting in conduit inspection. For example, the data acquisition device may include a magnetometer (e.g., scalar magnetometer, vector magnetometer, magnetograph, etc.) for measuring the strength and/or direction of a magnetic filed in the vicinity of the device. The data acquisition device may include an odometer for indicating the distance travelled by the device within the conduit 150. Other tools utilized in connection with the data acquisition device 110 may include one or more of the following: neutron-gamma devices for density detection of one or more regions proximate the conduit 150, high-frequency (e.g., 2-500 kHz) acoustic sources and receivers, H2S detectors, gas chromatographs, 3-D positioning devices or other tools. In addition, the data acquisition device may be equipped with one or more direct current or alternating current sources and receivers electrodes.

On-Board Data Storage

In conventional conduit inspection systems, during data acquisition, the acquired data is transmitted continually and in real-time from the underground conduit inspection device to the above-ground control system. See, e.g., Dae-Hyun Koo et al., "Innovative method for assessment of underground sewer conduit condition," Automation in Construction, Vol. 15, pp. 479-488 (2006); U.S. Pat. Nos. 7,131,344; 5,892,163, each of which is incorporated in its entirety by reference herein. However, in certain situations, such real-time, continual data transmission of substantially all of the acquired data creates practical problems for the operation of the conduit inspection system. For example, in certain circumstances, the conduit to be inspected is many hundreds or thousands of meters long. The amount of cable needed to provide sufficient bandwidth to allow substantially all of the acquired data to be transmitted continually in real-time over such distances (e.g., 100 kbps per GPR antenna) would be unduly heavy and/or thick so as to hinder the travel of the underground conduit inspection device within the conduit, both in the forward direction into and along the conduit and the backward direction out of and along the conduit. Systems implementing continual, real-time transmission of GPR data generally utilize a dedicated connection (e.g., an Ethernet connection). Therefore, a conventional inspection system may connect a data acquisition device or subsystem to an above-ground control subsystem using at least two separate data transmission cables, one for transmission of camera data, and another for transmission of GPR data. Such a configuration may be more bulky, heavy, or otherwise cumbersome than a configuration incorporating a single data transmission cable. In addition, a dedicated connection used for the GPR antenna(s) would further hinder the ability to provide the necessary cabling for inspection over significant distances. For example, the transmitted bandwidth of data transmission cables used in underground conduit-inspection devices decreases as the length of the cable increases. Therefore, the desired bandwidth for providing real-time transmission of significant amounts of GPR data may not be achievable beyond certain lengths of cable.

Certain embodiments described herein advantageously allow real-time, continual data transmission of a relatively small portion of the acquired data sufficient for monitoring the general operation of the underground conduit-inspection device 110 using the above-ground control subsystem 120. For example, certain systems disclosed herein do not transmit GPR data, or significant amounts of GPR data, continuously from within an underground conduit to an above-ground subsystem. Such embodiments may not suffer some or all of the disadvantages detailed above. In certain embodiments, only non-GPR data, such as video or other image data provided by one or more cameras (e.g., low-color resolution screen information), is provided in real-time from within the underground conduit to a location above ground. Compared to GPR data, such data generally requires less bandwidth. In addition, cables or tethers that do not require transmission of GPR data may be lighter and less bulky. Therefore, for reasons discussed above, such cables can be longer, thereby allowing for inspection of greater lengths of conduit.

Certain embodiments disclosed herein advantageously store the majority of the acquired data on the underground conduit inspection device 110 in real-time, rather than transmitting such data to an above-ground location, and allow access to the stored data once the conduit inspection device 110 is retrieved from within the conduit. The conduit-inspection system 100 may store all of the GPR data obtained from within the conduit 150 in a data storage subsystem 114 comprising an on-board storage device. Such embodiments may still transmit some amount of data in real-time to an above-ground location, such as video or other inspection data. Alternatively, the system 100 may store some fraction of the GPR data in an on-board storage device of the data storage subsystem 114. For example, 30, 50, 60, 75, 80 or 90 percent, or any other percentage of the GPR data may be stored on-board, while the remainder is transmitted to a location outside the conduit.

FIGS. 2 and 3 illustrate a profile view and a perspective view, respectively, of an example underground conduit-inspection system 200 in accordance with certain embodiments described herein. The system 200 is configured to move within a conduit substantially along a longitudinal axis of the conduit to inspect one or more portions of the conduit and/or surrounding materials. The system 200 comprises a data acquisition subsystem 210 and a data storage subsystem 220. The data acquisition subsystem 210 comprises one or more ground-penetrating radar (GPR) antennas 216 positioned within the conduit during the inspection. The one or more GPR antennas 216 are configured to emit GPR signals and to detect GPR signals reflected from the one or more portions of the conduit and/or the surrounding materials. The detected GPR signals reflected from the one or more portions of the conduit and/or the surrounding materials comprise inspection data indicative of the one or more portions of the conduit and/or the surrounding materials. The data storage subsystem 220 comprises a memory device 222 operatively coupled to the data acquisition subsystem 210 and located within the conduit during the inspection (e.g., proximate to the data acquisition subsystem 210). The data storage subsystem 220 is configured to receive the inspection data from the data acquisition subsystem 210.

In certain embodiments, all of the inspection data is stored within the data storage subsystem 220 (e.g., on the memory device 222) and none of the inspection data is transmitted to the above-ground control subsystem 120. In certain other embodiments, the system 200 is configured to transmit a first portion of the inspection data to the above-ground control subsystem 120 outside of the conduit during the inspection, either directly or via the data storage subsystem 220, and to store a second portion of the inspection data during the inspection (e.g., on the memory device 222 within the data storage subsystem 200). For example, some or all of the data provided by one or more cameras 218 may be transmitted to the above-ground control subsystem 120, while none of the data provided by one or more GPR antennas 216 is transmitted to the above-ground control subsystem 120, but is instead stored within the data storage subsystem 220. In one such example, during the inspection, one or more camera images are transmitted to the above-ground control subsystem 120, and control commands are sent from the above-ground control subsystem 120 to the conduit inspection device 110 within the conduit 150 (e.g., to control the conduit inspection device 110 so as to avoid obstacles within the conduit 150 shown by the camera images). As another example, some or all of the data provided by one or more cameras 218, as well as a portion of the data provided by one or more GPR antennas 216 (e.g., a small portion used for diagnostic purposes), may be transmitted to the above-ground control subsystem 120, while the majority of the data provided by the one or more GPR antennas 116 is stored within the data storage subsystem 220. The portion of the data stored within the data storage subsystem 220 can include the small amount of data that is transmitted to the above-ground control subsystem, as well as the portion of the data that is not transmitted to the above-ground control subsystem 120. During the inspection, in certain embodiments, the memory device 222 is configured to store a portion of the inspection data, e.g., a portion that is not transmitted to the computer system outside of the conduit. The data storage subsystem 220 is further configured to provide operational access to the memory device 222 and to the stored portion of the inspection data upon removal of the memory device 222 from within the conduit 150 after the inspection of the one or more portions of the conduit 150 and/or the surrounding materials.

As schematically illustrated by FIG. 2, in certain embodiments, the data acquisition subsystem 210 includes a motorized and remote-controllable robot 211 comprising a body portion 212 and a support portion 214. In an embodiment, the support portion 214 includes a travel-facilitating element 215 (e.g., wheel, tread, track, sled, flotation device, hover craft, etc.) configured to provide locomotion of the data acquisition subsystem 210 within the conduit. The data acquisition subsystem 210 may be equipped with one or more gyroscopes for detecting pitch, roll, and/or yaw of one or more components of the data acquisition subsystem 210. The data acquisition subsystem 210 may include one or more accelerometers for detecting acceleration of one or more components of the data acquisition subsystem 210. The support portion 214 may directly contact the wall of the conduit 150 during inspection (e.g., wheels that run along the bottom surface of the conduit 150, sled that slides along the bottom surface of the conduit 150, etc.), or may contact some other material located within the conduit 150 (e.g., a floatation device moving along the surface of a fluid or material located within the conduit). The data acquisition subsystem 210 further includes one or more GPR antennas 216 (examples of which are described above) mounted to the body portion 212 of the robot 211. In an embodiment, the one or more GPR antennas 216 are mounted to the body portion 212 by one or more arms 217, which may be remotely adjustable while the robot 211 is within the conduit 150 such that the distance between a GPR antenna 216 and the body portion 212 can be varied so as to position the one or more GPR antennas 216 to be in operational proximity to the surface of the conduit wall to be inspected. In certain embodiments, the data acquisition subsystem 210 further includes a trigger wheel 219, or odometer, which is configured to provide information relating to distance travelled by the robot 211 along the conduit 150. Such information may be useful in interpreting inspection data and/or determining a desirable antenna sampling rate.

In an embodiment, the underground conduit-inspection device 200 includes one or more cameras 218 (examples of which are described above), which may be mounted to the body portion 212 of the robot 211, or to any other feasible portion. In an embodiment, the underground conduit-inspection device 200 includes two cameras 218, one providing viewing in a first forward direction, with respect to a direction of travel along the longitudinal axis of the conduit 150, and another providing viewing in a direction substantially opposite of the first direction. In an embodiment, a camera 218 for inner-conduit viewing is a fish-eye lens camera. In an embodiment, the camera providing viewing in a first forward direction also provides visual information about the position and coupling with the conduit wall of one or more of the GPR antennas 116. In certain embodiments, a dedicated camera may be positioned such that it constantly monitors one or more antennas. Other dedicated cameras for particular purposes may also be used.

In an embodiment, camera data is transmitted to an above-ground computer system (e.g., the above-ground control subsystem 120) via a network connection (e.g., Ethernet). In certain embodiments, camera data is digitized and stored on the data storage subsystem 220 within the conduit 150. In such an embodiment, the screen capture may be sent to the above-ground control subsystem 120. By storing some amount of camera data on the data storage subsystem 220, bandwidth that otherwise would be dedicated to camera data transmission may become available for other uses.

In an embodiment, the data storage subsystem 220 includes one or more computer memory devices 222, such as random access memory ("RAM") and/or a read only memory ("ROM"), and/or a mass storage device, such as a hard drive, diskette, flash drive, or optical media storage device. The one or more memory devices 222 may comprise one or more solid-state drives (SSD) (e.g., 8 GB SSD or larger) memory cards (e.g., waterproof, replaceable), or other acceptable memory devices. The one or more memory devices 222 may provide the benefit of being able to store large amounts of GPR data on-board, thereby utilizing less transmission of data to an above-ground location during inspection. For example, the one or more memory devices 222 may be configured to store GPR data corresponding to lengths of 10, 100, 500 or 1000 meters or more of conduit, or any other amount of data that can be suitably stored in any of the systems disclosed herein. In an embodiment, the data storage subsystem 220 further comprises one or more computer processing units (not shown). Such processing units may operate in conjunction with the one or more memory devices 222.

In certain embodiments, the data storage subsystem 220 further comprises a container 224 that houses the one or more memory devices 222 and/or the computer processing units. The computer components housed within the container 224 are described in more detail with reference to FIG. 4. In an embodiment, the contents of the container 224 are sufficiently sealed by the container 224 from the environment outside the container 224 so as to prevent liquid, debris, or other material from entering the container 224 and disrupting operation of the one or more memory devices 222. The container may be made of any suitable material, such as metal or plastic. The container 224 is preferable constructed of material of sufficient strength and rigidity to adequately protect the internal components from structural damage. For example, the container 224 may be made from aluminum, among possibly other materials. In certain embodiments, the container 224 contains one or more heat sinks to aid in transferring thermal energy away from computer components. In addition, the container 224 may contain one or more active cooling devices (e.g., fans, thermoelectric devices, coolant systems, etc.) for reducing the temperature of components housed within the container. Other potential components that may be housed within the container 224 include, but are not limited to, one or more power supplies, gyroscopes or control units.

The data storage subsystem 220 further comprises one or more access ports 226, which provide operational access for signals, power, or both to and from the one or more memory devices 222 and/or the other computer components housed within the container 224. In an embodiment, the one or more access ports 226 are also configured to prevent entry of outside liquids, debris, or other material to the container 224. Access ports included in the data storage subsystem 220 may include Ethernet ports, USB ports, or any other desirable type of access port.

One or more components of the data storage subsystem 220 may be configured to wirelessly transmit data. For example, one or more components may be configured to wirelessly communicate information with a computing device located outside of the container 224. In certain embodiments, one or more components of the data storage subsystem 220 may communicate wirelessly with one or more other components of the data storage subsystem 220, or with one or more components of the data acquisition subsystem 210. Wireless communication may be implemented in accordance with any known standard or protocol, such as Bluetooth.

In an embodiment, the data storage subsystem 220 is operationally coupled to the robot 211. For example, the data storage subsystem 220 may be mounted to the body portion 212, or other portion, of the robot 211. In an embodiment, the data storage subsystem 220 is linked to the robot 211, as schematically illustrated in FIGS. 2 and 3. In an embodiment, the data storage subsystem 220 is positioned on a cart 240 that leads, trails, or runs alongside the robot 210. In an embodiment, the cart 240 includes one or more wheels, or other means facilitating travel through a conduit (examples of which are described above). In an embodiment, the cart 240 includes a floatation device.

Figure 4:
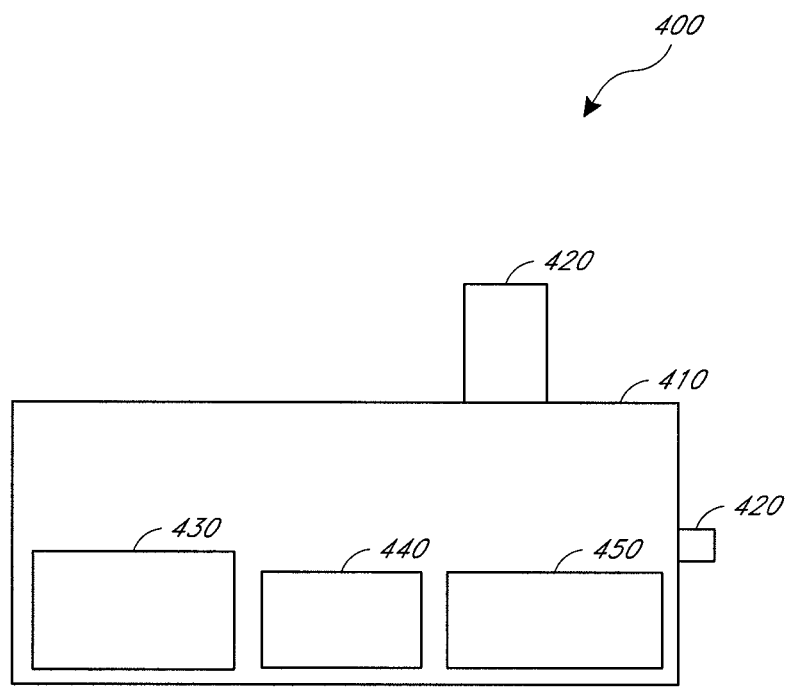
FIG. 4 provides a schematic of an example data storage device in accordance with certain embodiments described herein.

FIG. 4 illustrates a schematic view of an example data storage subsystem 400 in accordance with certain embodiments described herein. The data storage subsystem 400 of FIG. 4 can be used as the data storage subsystem 220 described above and shown in FIGS. 2 and 3. The data storage subsystem 400 includes a container 410, one or more access ports 420, a GPR control unit 430, an industrial computer 440, and a connector unit 450.

In an embodiment, the one or more access ports 420 provide operational access for input/output signals between one or more GPR antennas 216 and the data storage subsystem 400 and between the one or more GPR antennas 216 and the GPR control unit 430 during the data acquisition process. In an embodiment, one or more access ports 420 provide operational access for input/output signals between the data storage subsystem 400 and the one or more cameras 218 during the data acquisition process. The one or more access ports 420 of FIG. 4 can be used as the access ports 226 described above and shown in FIGS. 2 and 3.

In certain embodiments, the one or more access ports 420 provide operational access for input/output signals between the data storage subsystem 400 and the above-ground control subsystem 120 during the data acquisition process. For example, real-time, continual data transmission of a relatively small portion of the acquired data sufficient for monitoring the general operation of the underground conduit inspection system 200 using the above-ground control subsystem 120 is provided via one or more access ports 420 and a cable (not shown) operatively coupled to the one or more access ports 420 and the above-ground control subsystem 120. The bandwidth provided for such transmission may depend on the relevant cable length. For example, 38.4 kbps may be a suitable bandwidth in certain embodiments. In certain such embodiments, the majority of the acquired data is stored on the memory device 222 in real-time.

In certain embodiments, the access ports 420 are configured to allow access to the stored data on the memory device 222 once the data storage subsystem 400 is retrieved from within the conduit 150. In an embodiment, the data storage subsystem 400 provides an access port 420 configured to allow access to the stored data by a user while the data storage subsystem 400 is outside the conduit (e.g., after inspection). In this way, the acquired data can be retrieved for analysis without the constraint of the limited bandwidth available while the conduit inspection device is underground.

The GPR control unit 430 is configured to receive commands from the industrial computer 440 and to provide control signals to the various underground components of the conduit inspection system. In certain embodiments, the GPR control unit 430 controls the operation of one or more GPR antennas. For example, the GPR control unit 430 may control the activation and/or operational settings of one or more antennas, or any combination of operational elements of one or more GPR antennas (e.g., sampling rate, time window, sending and receiving of the GPR signal, frequency and/or strength of GPR signal, etc.).

The industrial computer 440 is configured to serve as a control and memory device, as described herein, and in certain embodiments, to provide some data manipulation capabilities in response to commands from the above-ground control system. In certain embodiments, the industrial computer 440 is a single-board, self-contained computer. However, more sophisticated computing devices may be included in the industrial computer 440, depending on the computing demands of the system. The industrial computer 440 may include, for example, a video card, or graphics card. The video card may assist in rendering or processing video images obtained by the data acquisition subsystem 112. In certain embodiments, the video card renders images from data from one or more GPR antennas for display. In certain embodiments, video or graphics hardware is integrated in on a motherboard of the industrial computer 440. In certain embodiments, the industrial computer 440 comprises the memory device 222 that stores at least a portion of the data generated by the data acquisition subsystem 210. Operational access to the industrial computer may be achieved via one or more data ports, such as USB ports, included in the industrial computer.

The connector unit 450 is configured to provide the desired electrical, optical, or other connections for transmission of signals among two or more of the components of the data storage subsystem 400. While the connector unit 450 is depicted as being located within the container 410 in FIG. 4, in certain embodiments, the connector unit 450 may be located outside the container 410. In certain embodiments, the connector unit 450 is located beneath the container 410. In certain embodiments, the connector unit 450 comprises a voltage converter utransformer (e.g., a "VT-300" manufactured by LiteFuze, Skokie, Ill.), which is connected to one or more components of the data storage subsystem 400 via one or more cables (e.g., twisted pair cabling). In certain embodiments, the connector unit 450 steps down voltage from a voltage source for use by one or more devices within the container 410. For example, the connector unit 450 may be configured to convert a 400 volt load down to useful range (e.g., 48 volts) for one or more devices.

In an embodiment, the GPR control unit 430 is operationally coupled to one or more GPR antennas 216 by one or more cables via one or more access ports 420. In certain embodiments, each of the internal modules of the data storage subsystem 400 (e.g., the GPR control unit 430, the industrial computer 440, the connector unit 430) is operationally coupled via one or more cables to one or more of the other internal modules, or to a data acquisition robot, antenna, or the above-ground control subsystem 120. In an embodiment, the data storage subsystem 400 does not include any external input/output access ports 420. In such an embodiment, access to the internal modules may be achieved wirelessly, or by opening the container 410. In an embodiment, the data storage subsystem 400 is connected to the above-ground control subsystem 120 via the access port 420 and a tether 118 (see FIG. 1).

Bi-Directional Antenna Mount

In conventional GPR conduit inspection systems, the GPR antenna is held rigidly in proximity to the surface being inspected. However, in certain situations, such rigid mounting can cause problems while the GPR antenna is being scanned across the surface. For example, in certain circumstances, the GPR antenna may encounter a protrusion, obstruction, or other discontinuity along the surface which hinders the GPR antenna from maintaining the desired positioning relative to the surface being inspected. The GPR antenna may also catch upon such discontinuities so that the movement of the underground data acquisition system along the longitudinal axis of the conduit or pipe is hindered, resulting in a disruption or termination of the inspection process, or even the underground data acquisition system becoming stuck within the conduit or pipe. Certain embodiments described herein advantageously allow the position of the GPR antenna adjust to reduce the probability of such problems occurring. Certain such embodiments also advantageously allow the position of the GPR antenna to be adjusted while the underground data acquisition system is moved in either the forward direction or the backward direction along the longitudinal axis of the conduit or pipe.

Figure 5:
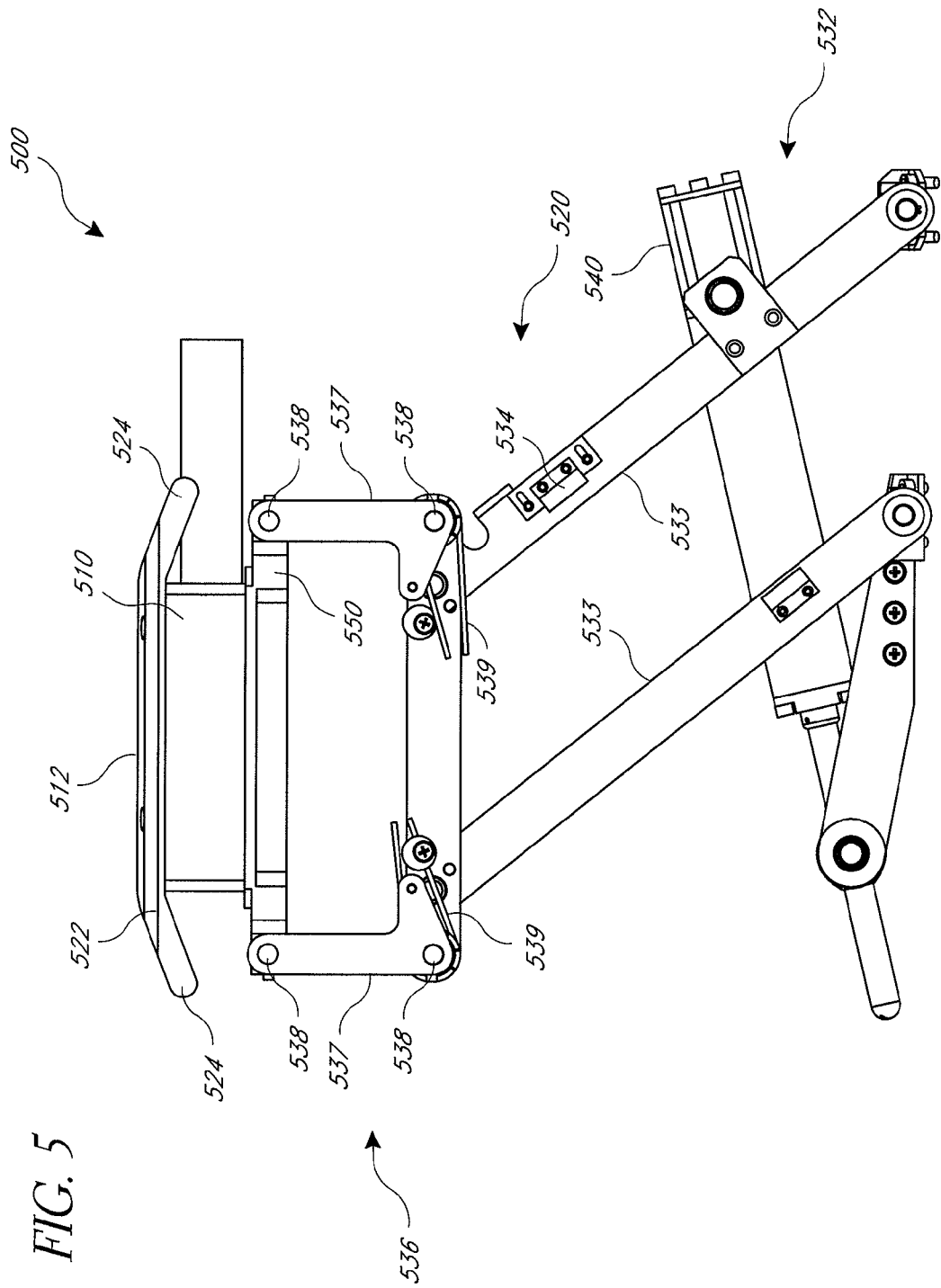
FIG. 5 provides a profile view of an example antenna mount for an underground conduit inspection system in accordance with certain embodiments described herein.
Figure 6:
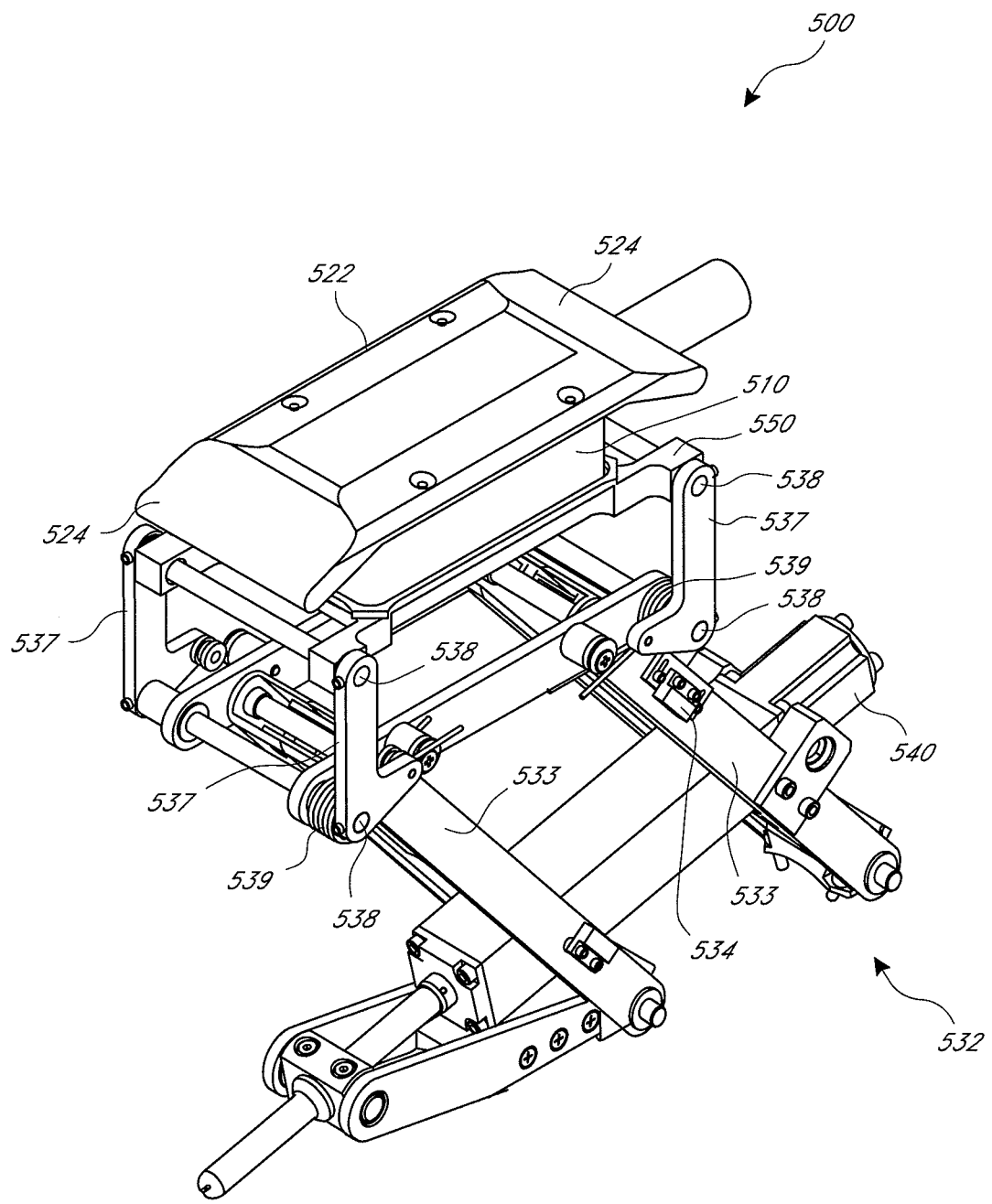
FIG. 6 provides a perspective view of an example antenna mount for an underground conduit inspection system in accordance with certain embodiments described herein.
Figure 7:
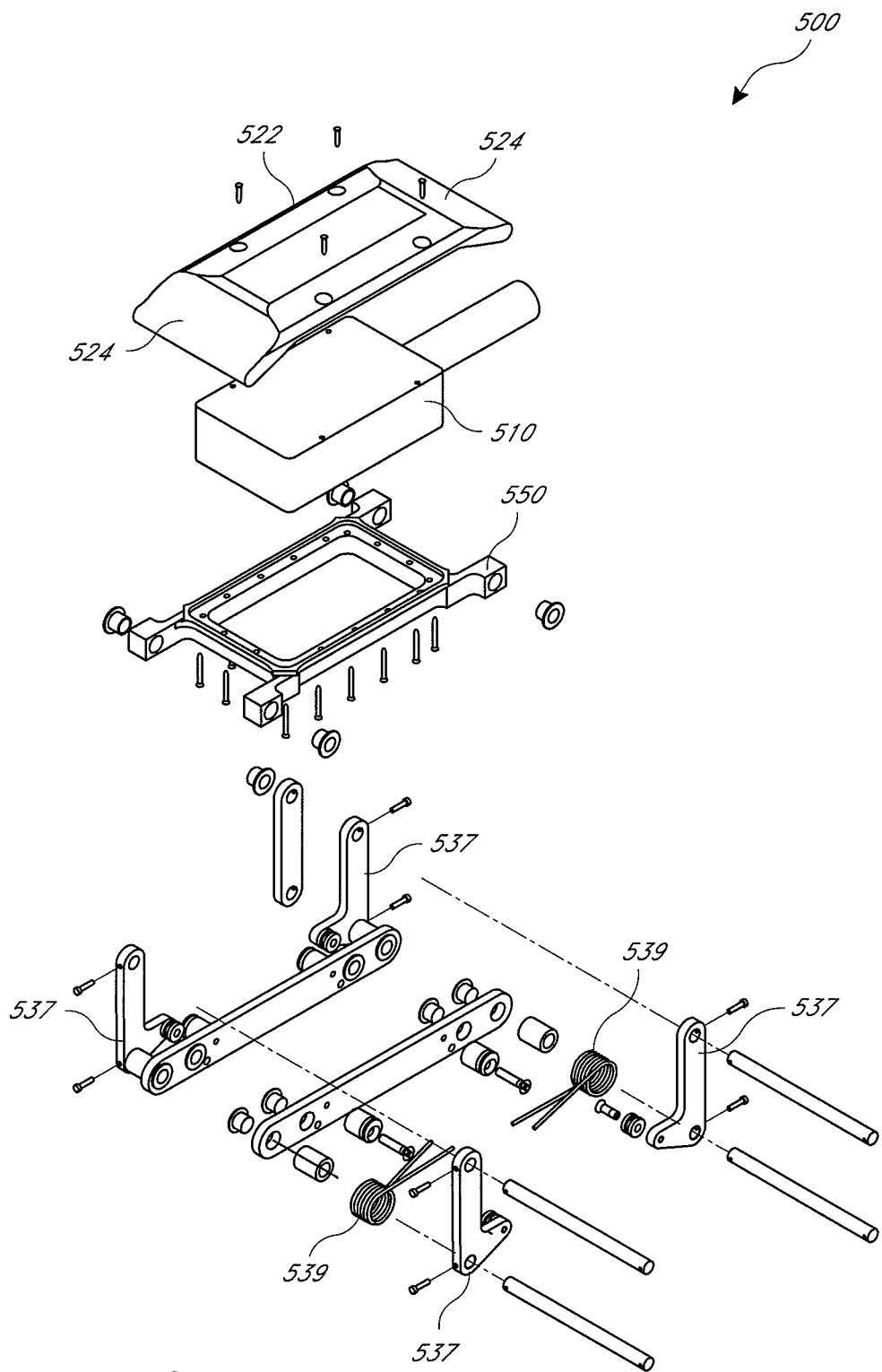
FIG. 7 provides a perspective exploded view of an example antenna mount for an underground conduit inspection system in accordance with certain embodiments described herein.

FIGS. 5 and 6 illustrates a profile view and perspective view, respectively, of an example antenna mount system 500 for an underground conduit inspection system in accordance with certain embodiments described herein. FIG. 7 provides a perspective exploded view of an example antenna mount system 500 for an underground conduit inspection system in accordance with certain embodiments described herein.

In certain embodiments, the antenna mount system 500 is configured to hold a ground-penetrating radar (GPR) antenna 510 in proximity to an inner surface of a conduit (e.g., a pipe) to be inspected while the GPR antenna 510 is moved along the surface during inspection of the conduit. The system 500 comprises a support structure 520 configured to adjust a position of the GPR antenna 510 in response to a force applied to the GPR antenna 510 by the inner surface of the conduit. In response to a drag or friction force between the surface and the GPR antenna 510, the support structure 520 adjusts the position of the GPR antenna 510 substantially along a direction of the drag or friction force. For example, where inspection of the conduit comprises orienting the GPR antenna 510 relative to a longitudinal axis of the conduit and moving the GPR antenna 510 in a first direction along the surface, a drag or friction force is applied by the surface to the GPR antenna 510 in a second direction substantially opposite to the first direction. In response to the drag or friction force, the support structure 520 adjusts the position of the GPR antenna 510 substantially along the second direction. In certain such embodiments in which inspection of the surface further comprises maintaining the orientation of the GPR antenna 510 relative to the longitudinal axis of the conduit and moving the GPR antenna 510 in the second direction along the surface, a drag or friction force is applied by the surface to the GPR antenna 510 in the first direction, and the support structure 520 adjusts the position of the GPR antenna 510 substantially along the first direction.

The antenna mount system 500 of FIG. 5 includes an antenna guide 522 and the support structure 520. In an embodiment, the antenna guide 522 includes an antenna surface 512 and one or more ramped end portions 524. Such ramped end portions 524 facilitate travel of the GPR antenna 510 along the surface being inspected in the presence of various types of obstructions or other features which may hinder the desired movement of the GPR antenna 510. In an embodiment, the antenna guide 522 is made of plastic, or other synthetic material. The antenna guide 522 may be made of a material that has characteristics which allow radar signals, or other signals, to propagate through it. In an embodiment, the antenna guide 522 is made of a material that causes essentially no attenuation in a radar wave passing through it.

The support structure 520 holds the GPR antenna 510 in proximity to a surface. The support structure 520 includes a proximal portion 532 mounted to the body portion 212 of the robot 211 and a distal portion 536 positionable towards the surface. The proximal portion 532 includes one or more arms 533, which connect the distal portion 536 to the body portion 212 of the robot 211. The proximal portion 532 further comprises an antenna-extension adjustment mechanism 540. The antenna-extension adjustment mechanism 540 applies a force to the one or more arms 533 and thereby effects a change in the distance between the GPR antenna 510 and the body portion 212 of the robot 211. In an embodiment, the one or more arms 533 include one or more sensors 534 that detect when the arms 533 are in a retracted position, that is, when the GPR antenna 510 is fully retracted away from the surface.

The distal portion 536 includes one or more arms 537, which connect the proximal portion 532 to an antenna frame 550 which secures the GPR antenna 510. The one or more arms 537 each includes at least one fulcrum 538 and at least one bi-directional biasing component 539. In an embodiment, each arm 537 includes two fulcrums 538, one at or near the point of connection between the arm 537 and the antenna frame 550, and another at or near the point of connection between the arm 537 and the proximal region 532, thereby allowing the antenna surface 512 to remain substantially parallel to the longitudinal axis of the conduit as the one or more arms 537 of the distal portion 536 rotate about a fulcrum 538. The bi-directional biasing component 539 applies a restoring force to the one or more arms 537 as they rotate about a fulcrum 538, thereby helping to maintain contact between the antenna surface 512, or antenna guide 520, and the surface being scanned. The bi-directional biasing component 539 may include, but is not limited to, a spring system, hydraulic system, pneumatic system, or the like.

In certain embodiments, when the robot 211 is moving in a forward direction along the longitudinal axis of the conduit and the antenna surface 512 is in contact with the surface being inspected, a drag or friction force is applied to the GPR antenna 512 by the surface in a direction generally opposite to the forward direction (e.g., the backward direction). The antenna mount system 500 is responsive to this drag or friction force by having the arms 537 rotate about the fulcrums 538 such that the GPR antenna moves in the backward direction while maintaining the orientation of the antenna surface 512 relative to the surface being inspected. The bi-directional biasing components 539 apply a restoring force to the arms 537 such that the antenna surface 512 is pressed towards the surface being inspected. Similarly, when the robot 211 is moving in the backward direction along the longitudinal axis of the conduit and the antenna surface 512 is in contact with the surface being inspected, a drag or friction force is applied to the GPR antenna 512 by the surface in the backward direction. The antenna mount system 500 is responsive to this drag or friction force by having the arms 537 rotate about the fulcrums 538 such that the GPR antenna moves in the forward direction while maintaining the orientation of the antenna surface 512 relative to the surface being inspected. The bi-directional biasing components 539 apply a restoring force to the arms 537 such that the antenna surface 512 is pressed towards the surface being inspected. Thus, upon contacting a discontinuity along the surface being inspected while the robot 211 is moving in either the forward direction or backward direction, the antenna mount system 500 advantageously maintains the orientation of the antenna surface 512 relative to the surface being inspected.

Method of Bi-Directional Scanning

Conventional conduit inspection systems are only configured for data acquisition while the underground portion moves in a single direction along the conduit. Even if such conventional systems were used to scan in two directions (e.g., in the forward and backward directions), such conventional systems are limited to having the GPR antennas at the same positions in both scans. Certain embodiments described herein advantageously modify the positions of the one or more GPR antennas between scans in the forward and backward directions, thereby providing additional data not provided by conventional systems.

Figure 8:
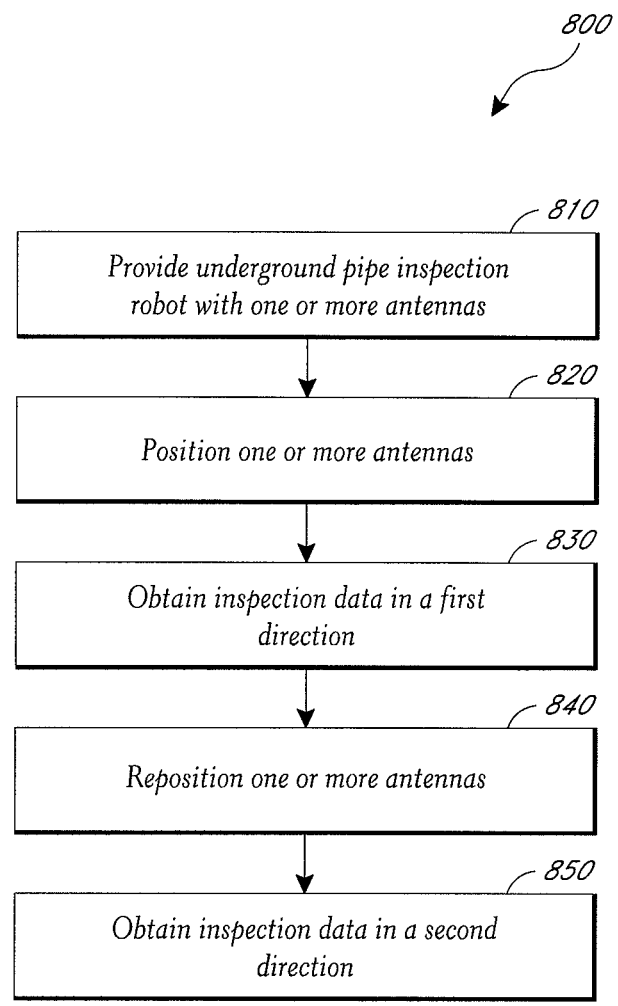
FIG. 8 illustrates an example process for bi-directional underground conduit inspection in accordance with certain embodiments described herein.

FIG. 8 illustrates an example bi-directional underground conduit or pipe inspection process 800 in accordance with certain embodiments described herein. The process 800 comprises providing a robot with one or more ground-penetrating radar (GPR) antennas in an operational block 810. The process 800 further comprises placing the one or more GPR antennas at corresponding first positions along the periphery of an inside surface of a conduit or pipe in an operational block 820. The process 800 further comprises obtaining inspection data using the one or more GPR antennas at the corresponding first positions as the robot travels in a first direction substantially along a longitudinal axis of the conduit or pipe being inspected in an operational block 830. The process 800 further comprises repositioning the one or more GPR antennas to be at corresponding second positions in an operational block 840. The process 800 further comprises obtaining inspection data using the one or more GPR antennas at the corresponding second positions as the robot travels in a second direction substantially along the longitudinal axis of the conduit being inspected, the second direction substantially opposite to the first direction in an operational block 850.

Block 810 includes providing a robot for underground conduit or pipe inspection with one or more GPR antennas. In certain embodiments, the robot and GPR antennas are configured as described herein.

Figure 9:
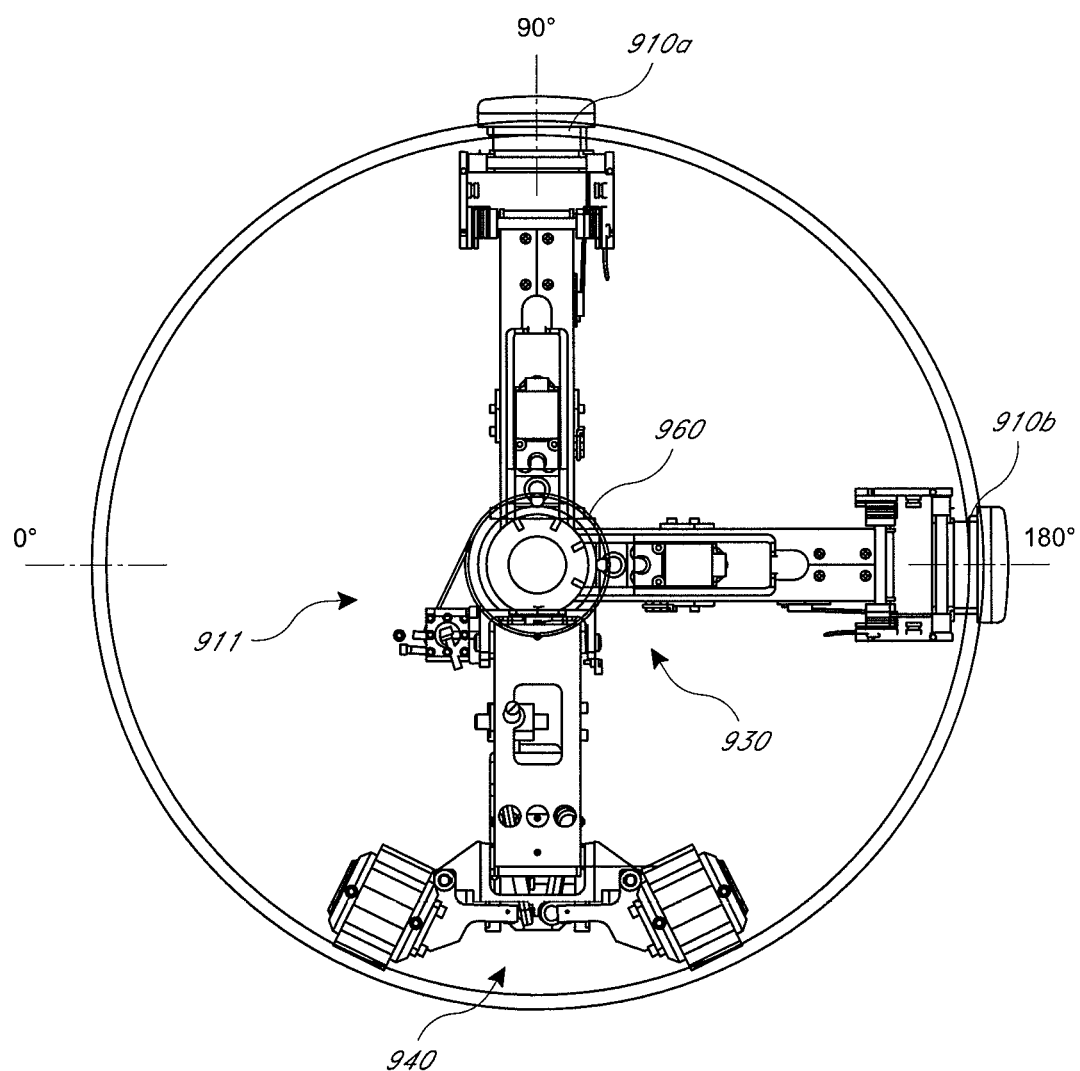
FIG. 9 illustrates an example antenna configuration for bi-directional underground conduit inspection in accordance with certain embodiments described herein.

At block 820, the one or more GPR antennas are positioned in a first configuration. For example, as schematically illustrated in FIG. 9, the robot 911 comprises two GPR antennas 910*a*, 910*b* which are placed at corresponding first positions (e.g., the 90-degree and 180-degree positions, respectively, as shown in FIG. 9) along a circumferential line in a cross-sectional view of the conduit. In certain other embodiments, one, two, or more GPR antennas 910 are positioned at other first angular positions (e.g., −45, −30, −20, −10, 0, 10, 20, 30, 40, 45, 50, 60, 70, 80, 90, 100, 110, 120, 130, 140, 150, 160, 170, 180, 190, 200, 210, 220, 225, 230, 245, 250, 260, 270, 285, 300, 315 degrees, or positions between these angular positions) along the circumferential line. While FIG. 9 illustrates two GPR antennas at first angular positions approximately 90 degrees relative to one other, other embodiments including two or more GPR antennas 910 can have the GPR antennas 910 at other angles relative to one another.

At block 830, inspection data is obtained as the robot 911 moves in a first direction substantially along the longitudinal axis of the conduit or pipe (e.g., substantially perpendicular to the circumferential line). During such data acquisition, the first GPR antenna 910*a* obtains data along a line corresponding to its first angular position (e.g., 90-degree position) and substantially parallel to the longitudinal axis of the conduit, and the second GPR antenna 910*b* obtains data along a line corresponding to its first angular position (e.g., 180-degree position) and substantially parallel to the longitudinal axis of the conduit.

At block 840, after obtaining inspection data while moving in the first direction, the one or more GPR antennas 910 are reconfigured or repositioned, such that at least one GPR antenna 910 is at a second angular position along the circumferential line. For example, in certain embodiments, the first GPR antenna 910*a* (after lowering) is repositioned at a second angular position (e.g., the 0-degree position) and the second GPR antenna 910*b* after lowering) is repositioned at a second angular position (e.g., the 90-degree position). For example, in certain embodiments, the antennas are lowered or retracted away from the surface being inspected prior to repositioning. The repositioning of the antennas in certain embodiments is performed while the robot 911 remains within the conduit or pipe, and is not withdrawn from the conduit or pipe prior to obtaining the inspection data as the robot 911 moves in the second direction, as described below. In certain embodiments, the one or more GPR antennas 910 are repositioned by rotating the GPR antennas by some amount circumferentially with respect to the longitudinal axis of the conduit or pipe being inspected. In certain embodiments, the GPR antennas 910 are positioned at other angular second positions (e.g., −45, −30, −20, −10, 0, 10, 20, 30, 40, 45, 50, 60, 70, 80, 90, 100, 110, 120, 130, 140, 150, 160, 170, 180, 190, 200, 210, 220, 225, 230, 245, 250, 260, 270, 285, 300, 315 degrees, or positions between these angular positions) along the circumferential line. Other embodiments including two or more GPR antennas 910 can have the GPR antennas 910 at other second angular positions which are less than, more than, or equal to 90 degrees relative to one another.

At block 850, inspection data is obtained as the robot 911 moves in a second direction, substantially opposite to the first direction of travel and substantially along the longitudinal axis of the conduit or pipe (e.g., substantially perpendicular to the circumferential line). During such data acquisition, the first GPR antenna 910*a* obtains data along a line corresponding to its second angular position (e.g., 0-degree position) and substantially parallel to the longitudinal axis of the conduit, and the second GPR antenna 910*b* obtains data along a line corresponding to its second angular position (e.g., 90-degree position) and substantially parallel to the longitudinal axis of the conduit.

The robot 911 of FIG. 9 includes a body portion 930 and a travel-facilitating portion 940, which is configured to allow for advancement of the robot 911 within the conduit. In an embodiment, the travel-facilitating portion 940 could include a wheel, tread, sled, floatation device or the like. In an embodiment including a flotation device, the travel-facilitating portion 940 may further comprise one or more paddle elements or the like. The travel-facilitating portion 940 also provides support for the body portion 930 of the robot 911. In an embodiment, the body portion 930 of the robot 911 is extendable, such that the distance between the center of the body portion 930 and the travel-facilitating portion 940 can vary. In an embodiment, the body portion 930 of the robot 911 is extended such that the center of the body portion 930 is substantially near the center of the conduit or pipe with respect to a plane perpendicular to the longitudinal axis of the conduit or pipe.

In certain embodiments, the body portion 930 includes a rotating mechanism 960, which is capable of rotating at least one of the GPR antennas 910 about the body portion 930. The rotating mechanism 960 may include a motor or any other means of applying a rotational force to a GPR antenna 910 or to a portion of the robot 911 upon which the GPR antenna 910 is mounted.

Figure 10:
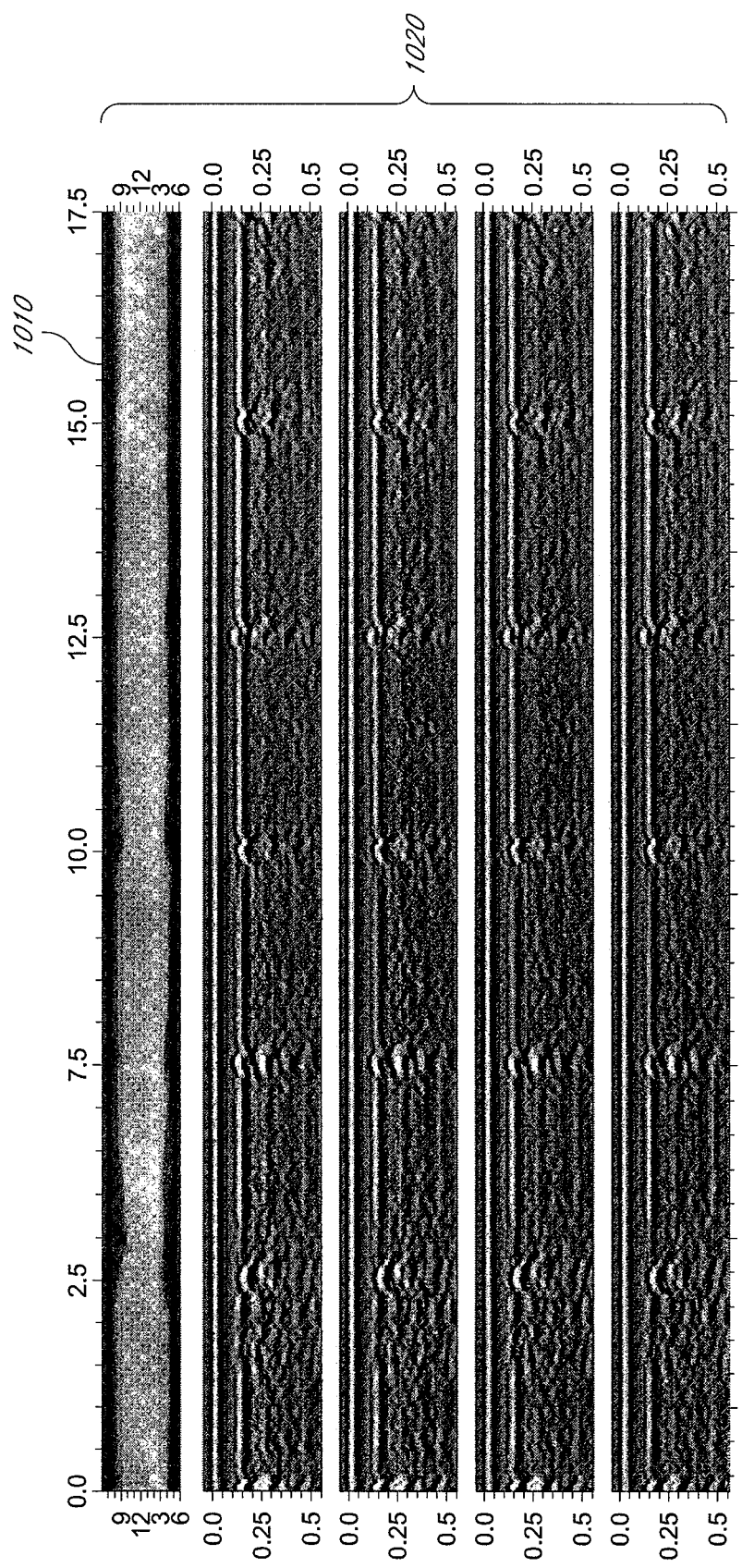
FIG. 10 illustrates an example data presentation of underground pipe inspection data in accordance with certain embodiments described herein.

FIG. 10 illustrates an example data presentation relating to data obtained from an underground conduit-inspection system in accordance with certain embodiments described herein. The video data 1010 acquired using the cameras of the robot is shown in an flattened or fold-out (i.e., "snakeskin") view in which the abscissa corresponds to positions along the longitudinal axis of the conduit and the ordinate corresponds to angular positions (e.g., 0, 60, 120, 180 degrees or 12-o'clock, 3-o'clock, 6-o'clock, and 9-o'clock positions) along the circumferential line. The GPR data 1020 acquired using the GPR antennas is shown in a view with the abscissa corresponding to positions along the longitudinal axis of the conduit and the ordinate corresponding to distance from the GPR antenna. The abscissa of the video data 1010 and the abscissa of the GPR data 1020 are aligned to facilitate identification of corresponding features in the two data sets. As shown in FIG. 10, the GPR data 1020 of certain embodiments comprises four data scans comprising data obtained from two GPR antennas in two corresponding first positions while the robot moves in the forward direction, and in two corresponding second positions while the robot moves in the backward direction.

Figure 11:
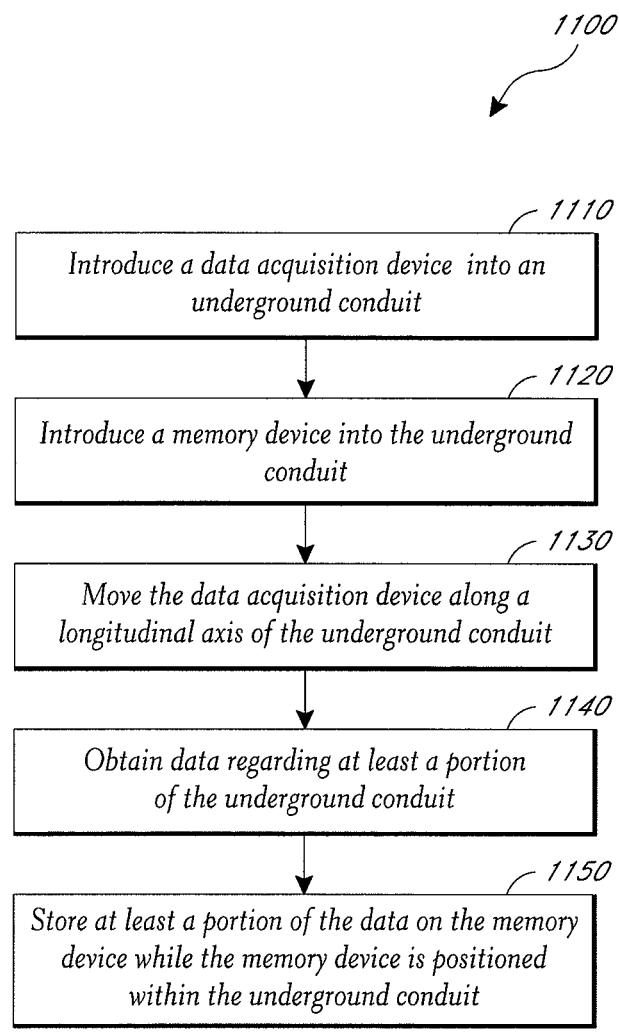
FIG. 11 illustrates a flowchart for a method of inspecting an underground conduit from within.

FIG. 11 illustrates a flow chart for a method of inspecting an underground conduit from within. The method 1100 includes introducing a data acquisition device into an underground conduit in an operational block 1110. The underground conduit may be an underground sewer conduit, or other underground conduit, and may be made of concrete, or other materials. A memory device is also introduced into the underground conduit in an operational block 1120. In an embodiment, the data acquisition device comprises one or more GPR antennas configured to analyze the walls of the conduit and to obtain data related thereto. The data may include GPR data and/or image data obtained by one or more image-capturing devices. The image data may include visual image data, or may correspond to images outside the visible spectrum (e.g., infrared). The memory device may be configured to store at least a portion GPR data obtained by the data acquisition device.

In certain embodiments, the method includes transmitting at least a portion of data to an above-ground location during inspection. Such data may include data obtained from one or more image-capturing devices (e.g., video or still-image cameras).

The method 1100 also includes moving or advancing the data acquisition device along a longitudinal axis of the underground conduit in an operational block 1130. The data acquisition device may be moved along the underground conduit in order to traverse a portion of the conduit to which corresponding inspection data is desired. Data corresponding to, or regarding a portion of the underground conduit is obtained in operational block 1140. In certain embodiments, the data obtained provides information relating to the condition of the conduit, and may reveal cracks or other imperfections in the conduit or outside of the conduit wall. The method includes storing at least a portion of the data on the memory device while the memory device is positioned within the underground conduit in an operational block 1150. In certain embodiments, the data acquisition device obtains GPR data, all or part of which is stored on the memory device. In certain embodiments, the method includes retrieving at least a portion of the stored data from the memory device. For example, the data may be retrieved by the user after the memory device has been removed from the conduit, or may be retrieved after the process of data acquisition is completed and while the memory device is still positioned within the conduit.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Additionally, the skilled artisan will recognize that any of the above-described methods can be carried out using any appropriate apparatus. Further, the disclosure herein of any particular feature, aspect, method, property, characteristic, quality, attribute, element, or the like in connection with an embodiment can be used in all other embodiments set forth herein. Thus, it is intended that the scope of the present invention herein disclosed should not be limited by the particular disclosed embodiments described above.

What is claimed is:

1. A system for inspecting an underground conduit from within, the system comprising:
    a data acquisition subsystem configured to be placed within the conduit and to move along at least a portion of the conduit to generate ground-penetrating radar data regarding the portion of the conduit while within the conduit, the data acquisition subsystem comprising:
        one or more antennas configured to be in contact with an inner surface of the conduit while the data acquisition subsystem moves along the portion of the conduit;
        a support structure configured to adjust a position of the one or more antennas while the data acquisition subsystem moves along the portion of the conduit, the position adjusted in response to a force applied to the one or more antennas by the inner surface of the conduit; and
        at least one camera configured to monitor the position of the one or more antennas; and
    a data storage subsystem configured to be placed within the conduit and to move along the conduit, the data storage subsystem configured to receive and store at least a portion of the ground-penetrating radar data while within the conduit from the data acquisition subsystem for retrieval after the data acquisition subsystem has moved along the portion of the conduit.

2. The system of claim 1, wherein the data storage subsystem stores a substantial fraction of the ground-penetrating radar data.

3. The system of claim 1, wherein the data storage subsystem stores at least thirty percent of the ground-penetrating radar data.

4. The system of claim 1, wherein the portion of the ground-penetrating radar data stored by the data storage subsystem corresponds to a length of the portion of the conduit, wherein the length is greater than at least ten meters.

5. The system of claim 1, wherein the data storage subsystem is configured to store data at a rate of at least 10 kilobytes per second.

6. The system of claim 1, wherein the data acquisition subsystem further comprises:
a body portion; and
a support portion configured to provide support for the body portion; and
the one or more antennas comprises:
at least one horn antenna configured to emit ground-penetrating radar; and
a mirror configured to adjustably reflect a signal from the at least one horn antenna towards the inner surface of the conduit.

7. The system of claim 6, wherein the at least one horn antenna comprises an ultra-wideband horn antenna.

8. The system of claim 1, further comprising an above-ground control subsystem that provides at least one control signal to the data acquisition subsystem, wherein the data acquisition subsystem is responsive to the at least one control signal to control one or more aspects of the data acquisition subsystem.

9. The system of claim 8, wherein at least one of the data acquisition subsystem and the data storage subsystem is tethered to the above-ground control system by a data conduit having a cross-sectional area of less than 0.2 square inches.

10. The system of claim 8, wherein at least one of the data acquisition subsystem and the data storage subsystem is tethered to the above-ground control system by a data conduit having a length of greater than 100 meters.

11. The system of claim 1, wherein at least one of the one or more cameras is a wide-spectrum camera.

12. The system of claim 1, wherein the data acquisition subsystem comprises a camera facing in a forward direction with respect to a direction of travel of the data acquisition device within the conduit, and a camera facing in a direction substantially opposite to the forward direction.

13. The system of claim 1, wherein the data acquisition subsystem is configured to generate the ground-penetrating radar data by emitting ground-penetrating radar signals from the one or more antennas while within the conduit and detecting reflected ground-penetrating radar signals within the conduit, the reflected ground-penetrating radar signals indicative of a wall of the conduit, materials surrounding the wall, or both.

14. The system of claim 13, wherein the data acquisition subsystem is configured to generate the ground-penetrating radar data by emitting ground-penetrating radar signals from the one or more antennas that penetrate a wall of the conduit from within the conduit and detecting at least a portion of the ground-penetrating radar signals that are reflected from material outside the wall.

15. A system for inspecting an underground conduit from within, the system comprising:
a data acquisition subsystem configured to be placed within the conduit and to move along at least a portion of the conduit to obtain data regarding the portion of the conduit, wherein the data acquisition subsystem comprises:
a body portion;
a support portion configured to be in direct physical contact with the conduit or with material within the conduit so as to provide support for the body portion;
one or more antennas configured to be adjustably positionable in response to a force applied to the one or more antennas by an inner surface of the conduit to remain in contact with the inner surface of the conduit during inspection of the conduit;
at least one camera configured to monitor a position of the one or more antennas; and
a data storage subsystem configured to be placed within the conduit and to move along the conduit, the data storage subsystem configured to receive and store at least a portion of the data from the data acquisition subsystem for retrieval after the data acquisition subsystem has moved along the portion of the conduit.

16. The system of claim 15, wherein the support portion comprises at least one travel-facilitating member configured to provide locomotion of the data acquisition subsystem along a longitudinal axis of the conduit.

17. The system of claim 16, wherein the at least one travel-facilitating member comprises at least one of the group consisting of: wheels, sleds, treads, tracks, hovercrafts, and flotation devices.

18. The system of claim 15, wherein the one or more antennas are adjustably mounted to the body portion so as to controllably vary a distance between the one or more antennas and the inner surface of the conduit.

19. An apparatus for inspecting an underground conduit from within, the apparatus comprising:
a data acquisition device configured to be placed within the conduit and to move along a first portion of the conduit to generate ground-penetrating radar data regarding the first portion of the conduit while within the conduit, the data acquisition device comprising:
one or more antennas configured to be in contact with an inner surface of the conduit during inspection of the conduit;
a support structure configured to adjust a position of the one or more antennas while the data acquisition device moves along the first portion of the conduit, the position adjusted in response to a force applied to the one or more antennas by the inner surface of the conduit; and
at least one camera configured to monitor the position of the one or more antennas; and
a memory device configured to:
be positioned within the conduit and operationally coupled to the data acquisition device while positioned within the conduit;
travel along a second portion of the conduit; and
store at least a portion of the ground-penetrating radar data while within the conduit from the data acquisition device for retrieval after the data acquisition device has moved along the first portion of the conduit.

20. The apparatus of claim 19, wherein the memory device is contained within a container that is liquid-tight.

21. The apparatus of claim 20, wherein the memory device is configured to provide wireless accessibility to data stored by the memory device.

22. The apparatus of claim 20, wherein the container comprises a lid configured to be manually removable to facilitate data transmission by providing physical access to the memory device.

23. The apparatus of claim 19, wherein the second portion of the conduit is coextensive with at least some of the first portion of the conduit.

24. A method for inspecting an underground conduit from within, the method comprising:
   introducing a data acquisition device into the underground conduit, the data acquisition device comprising:
      one or more antennas configured to be in contact with an inner surface of the conduit during inspection of the conduit;
      a support structure configured to adjust a position of the one or more antennas while the data acquisition device moves along a portion of the conduit, the position adjusted in response to a force applied to the one or more antennas by the inner surface of the conduit; and
      at least one camera configured to monitor the position of the one or more antennas;
   introducing a memory device into the underground conduit;
   moving the data acquisition device along a longitudinal axis of the underground conduit;
   obtaining ground-penetrating radar data regarding at least a portion of the underground conduit using the data acquisition device within the underground conduit while the one or more antennas are in contact with the inner surface of the conduit; and
   storing at least a portion of the ground-penetrating radar data on the memory device while the memory device is positioned within the underground conduit.

25. The method of claim 24, further comprising transmitting a second portion of the ground-penetrating radar data to a location outside of the underground conduit.

* * * * *